United States Patent [19]
Woychik et al.

[11] Patent Number: 6,090,554
[45] Date of Patent: Jul. 18, 2000

[54] EFFICIENT CONSTRUCTION OF GENE TARGETING VECTORS

[75] Inventors: Richard Woychik, Beechwood, Ohio; David Garfinkel, Frederick, Md.

[73] Assignee: Amgen, Inc., Thousand Oaks, Calif.

[21] Appl. No.: 08/963,602

[22] Filed: Oct. 31, 1997

[51] Int. Cl.[7] ................................................. C12Q 1/68
[52] U.S. Cl. ........................................ 435/6; 435/172.3
[58] Field of Search ..................................... 435/6, 172.3

[56] References Cited

U.S. PATENT DOCUMENTS

| 5,530,178 | 6/1996 | Mak | 800/2 |
|---|---|---|---|
| 5,547,862 | 8/1996 | Meador et al. | 435/91.3 |
| 5,625,122 | 4/1997 | Mak | 800/2 |

FOREIGN PATENT DOCUMENTS

WO 95/14769   1/1995   WIPO.

OTHER PUBLICATIONS

Ausubel et al., (Eds.), in *Current Protocols in Molecular Biology*, Chapter 5, "Construction of Recombinant DNA Libraries," John Wiley & Sons, Inc. p. 5.0.1–5.11.2 (1987).
Barinaga, M., "Knockout Mice Offer First Animal Model for CF," *Science*, 257:1046–1047 (1992).
Baudin, A. et al., "A simple and efficient method for direct gene deletion in *Saccharomyces cerevisiae*," *Nucleic Acids Research*, 21(14):3329–3330(1993).
Bollag, R.J. et al., "Homologous Recombination in Mammalian Cells," *Annu. Rev. Genet.*, 23:199–225 (1989).
Bradley, A. et al., "Embryo–Derived Stem Cells: A Tool for Elucidating the Developmental Genetics of the Mouse," *Current Topics in Developmental Biology*, 20:357–371 (1986).
Chalfie, M. et al., "Green Fluorescent Protein as a Marker for Gene Expression," *Science*, 263:802–805 (1994).
Chen, C. et al., "Abnormal Fear Response and Aggressive Behavior in Mutant Mice Deficient for α–Calcium–Calmodulin Kinase II," *Science*, 266:291–294 (1994).
Christianson, T.W. et al., "Multifunctional yeast high–copy–number shuttle vectors," *Gene*, 110:119–122 (1992).
Dopf, J. et al., "Deletion mapping of the *Aequorea victoria* green fluorescent protein," *Gene*, 173:39–44 (1996).
Dorin, J.R. et al., "Successful targeting of the mouse cystic fibrosis transmembrane conductance regulator gene in embryonal stem cells," *Transgenic Research*, 1:101–105 (1992).
Fung–Leung, W–P et al., "CD8 Is Needed for Development of Cytotoxic T Cells but Not Helper T Cells," *Cell*, 65:443–449 (1991).
Geitz, R.D. et al., "High Efficiency Transformation with Lithium Acetate," In *Molecular Genetics of Yeast, A Practical Approach*, J.R. Jonston, Ed., pp. 121–134 (1995).
Gu, H. et al., "Deletion of a DNA Polymerase β Gene Segment in T Cells Using Cell Type–Specific Gene Targeting," *Science*, 265:103–106(1994).

Guthrie, C. et al., Eds. in *Methods in Enzymology: Guide to Yeast Genetics and Molecular Biology*, vol. 194, Academic Press, pp. 182–187, 239–251, 319–329, 373–388, and 389–398 (1991).
Hamer, R.E. et al., "Production of transgenic rabbits, sheep and pigs by microinjection," *Nature*, 315:680–683 (1985).
Hanks, M. et al., "Rescue of the En–1 Mutant Phenotype by Replacement of En–1 with En–2," *Science*, 269:679–682 (1995).
Hoffman, C.S. et al., "A ten–minute DNA preparation from yeast efficiently releases autonomous plasmids for transformation of *Escherichia coli*," *Gene*, 57:267–272 (1987).
Hogan et al. in *Manipulating the Mouse Embryo: A Laboratory Manual*, Cold Spring Harbor Laboratory Press, Cold Spring Harbor New York, pp. 91–149, 153–197, and 247–267 (1986).
Joyner, A.L. et al., "Production of a mutation in mouse En–2 gene by homologous recombination in embryonic stem cells," *Nature*, 338:153–156 (1989).
Joyner, A.L., (ed.) in *Gene Targeting: A Practical Approach*, IRL Press, Oxford University Press, New York, pp. 107–144 and 147–178 (1993).
Knudsen, C.M. et al., "Bax–Deficient Mice with Lymphoid Hyperplasia and Male Germ Cell Death," *Science*, 270:96–99 (1995).
Koller, B.H. et al., "Toward an animal model of cystic fibrosis: Targeted interruption of exon 10 of the cystic fibrosis transmembrane regulator gene in embryonic stem cells," *Proc. Natl. Acad. Sci., USA*, 88:10730–10734(1991).
Lorenz, M.C. et al., "Gene disruption with PCR products in *Saccharomyces cerevisiae*," *Gene*, 158:113–117 (1995).
Luo, Y. et al., "A Novel Method for Monitoring *Mycobacterium bovis* BCG Trafficking with Recombinant BCG Expressing Green Fluorescent Protein," *Clinical Diagnostic Laboratory Immunology*, 3(6):761–768 (1996).
Lutz, C.T. et al., "Syrinx 2A: An improved λ phage vector designed for screening DNA libraries by recombination in vivo," *Proc. Natl. Acad. Sci., USA*, 84:4379–4383 (1987).
Manivasakam, P. et al., "Micro–homology mediated PCR targeting in *Saccharomyces cerevisiae*," *Nucleic Acids Research*, 23(14):2799–2800 (1995).
Marx, J., "Knocking Genes In Instead of Out," *Science*, 269:636 (1995).
Michaud, E.J. et al., "The embryonic lethality of homozygous lethal yellow mice ($A^y/A^y$) is associated with the disruption of a novel RNA–binding protein," *Genes & Development*, 7:1203–1213 (1993).
Miki, Y. et al., "A Strong Candidate for the Breast and Ovarian Cancer Susceptibility Gene BRCA1," *Science*, 266:66–71 (1994).

(List continued on next page.)

Primary Examiner—James Ketter
Attorney, Agent, or Firm—Marshall, O'Toole, Gerstein, Murray & Borun

[57] ABSTRACT

The present invention is directed to methods for producing or obtaining gene targeting constructs by way of homologous recombination in host cells and to targeting constructs produced by those methods. The invention is also directed to transgenic animals having targeted mutations introduced into the cells of the animal using the targeting constructs of the invention.

26 Claims, 12 Drawing Sheets

OTHER PUBLICATIONS

Mansour, S.L. et al., "Disruption of the proto–oncogene int–2 in mouse embryo–derived stem cells: a general strategy for targeting mutations to non–selectable genes," *Nature*, 336:348–352 (1988).

Moyer, J.H. et al., "Candidate Gene Associated with a Mutation Causing Recessive Polycystic Kidney Disease in Mice," *Science*, 264:1329–1333 (1994).

Oldenbburg, K.R. et al., "Recombination–mediated PCR––directed plasmid construction in vivo in yeast," *Nucleic Acids Research*, 25(2):451–452 (1997).

Orr–Weaver, T.L. et al., "Fungal Recombination," *Microbiological Reviews*, 49(1):33–58 (1985).

Robertson, E.J. (ed.) in *Teratocarcinomas and embryonic stem cells, a practical approach*, IRL Press, Washington D.C., pp. 113–181 (1987).

Sambrook et al., *Molecular Cloning: A Laboratory Manual*, section p. 1.19, 1.74–1.75, 2.6, 8.2–8.86, and 9.2–9.58 Cold Spring Harbor Laboratories (1989).

Seed, B., "Purification of genomic sequences from bacteriophage libraries by recombination and selection in vivo," *Nucleic Acids Research*, 11(8):2427–2445 (1983).

Sikorski, R.S. et al., "A System of Shuttle Vectors and Yeast Host Strains Designed for Efficient Manipulation of DNA in *Saccharomyces cerevisiae,*" *Genetics*, 122:19–27 (1989).

Silva, A.J. et al., "Deficient Hippocampal Long–Term Potentiation in α–Calcium–Calmodulin Kinase II Mutant Mice," *Science*, 257:201–206 (1992).

Snouwaert, J.N. et al., "An Animal Model for Cyctic Fibrosis Made by Gene Targeting," *Science*, 257:1083–1088 (1992).

Soriano et al., "Targeted Disruption of the c–src Proto–Oncogene Leads to Osteopetrosis in Mice," *Cell*, 64:693–702 (1991).

Storck, T. et al., "Rapid construction in yeast of complex targeting vectors for gene manipulation in the mouse," *Nucleic Acids Research*, 24(22):4594–4596 (1996).

Tavtigian, S.V. et al., "The complete BRCA2 gene and mutations in chromosome 13q–linked kindreds," *Nature Genetics*, 12:333–337 (1996).

Thomas, K.R. et al., "Site–Directed Mutagenesis by Gene Targeting in Mouse Embryo–Derived Stem Cells," *Cell*, 51:503–512 (1987).

Travis, J. "Scoring a Technical Knockout in Mice," *Science*, 256:1392–1394 (1992).

Veis, D.J. et al., "Bcl–2–Deficient Mice Demonstrate Fulminant Lymphoid Apoptosis, Polycystic Kidneys, and Hypopigmented Hair,"*Cell*, 75:229–240 (1993).

Wang, N. et al., "Impaired Energy Homeostasis in C/EBPα Knockout Mice," *Science*, 269:1108–1112 (1995).

Zhang, Y. et al., "Positional cloning of the mouse obese gene and its human homologue," *Nature*, 372: 425–432 (1994).

Ausubel et al., (Eds.), in *Current Protocols in Molecular Biology*, Chapter 5, "Construction of Recombinant DNA Libraries," John Wiley & Sons, Inc. pp. 5.0.1–5.11.2 (1987).

Barinaga, M., "Knockout Mice Offer First Animal Model for CF," *Science*, 257:1046–1047 (1992).

Baudin, A. et al., "A simple and efficient method for direct gene deletion in *Saccharomyces cerevisiae,*" *Nucleic Acids Research*, 21 (14): 3329–3330 (1993).

Bollag, R.J. et al., "Homologous Recombination in Mammalian Cells," *Annu. Rev. Genet.*,23:199–225 (1989).

Bradley, A. et al., "Embryo–Derived Stem Cells: A tool for Elucidating the Developmental Genetics of the Mouse," *Current Topics in Developmental Biology*, 20:357–371 (1986).

Chalfie, M. et al., "Green Fluorescent Protein as a Marker for Gene Expression," *Science*, 263:802–805 (1994).

Chen, C. et al., "Abnormal Fear Response and Aggressive Behavior in Mutant Mice Deficient for α–Calcium–Calmodulin Kinase II," *Science*, 266:291–294 (1994).

Christianson, T. W. et al., "Multifunctional yeast high–copy–number shuttle vectors," *Gene*, 110:119–122 (1992).

Dopf, J. et al., "Deletion mapping of the *Aequorea victoria* green fluorescent protein," *Gene*, 173:39–44 (1996).

Dorin, J.R. et al., "Successful targeting of the mouse cystic fibrosis transmembrane conductance regulator gene in embryonal stem cells," *Transgenic Research*, 1:101–105 (1992).

Fung–Leung, W–P et al., "CD8 is Needed for Development of Cytotoxic T Cells but Not Helper T Cells," *Cell*, 65:443–449 (1991).

Geitz, R. D. et al., "High Efficiency Transformation with Lithium Acetate," In *Molecular Genetics of Yeast, A Practical Approach*, J.R. Jonston, Ed., pp. 121–134 (1995).

Gu, H. et al., "Deletion of a DNA Polymerase β Gene Segment in T Cells Using Cell Type–Specfic Gene Targeting," *Science*, 265:103–106(1994).

Guthrie, C. et al., Eds. in *Methods in Enzymology: Guide to Yeast Genetics and Molecular Biology*, Volume 194, Academic Press, pp. 182–187, 239–251, 319–329, 373–388, and 389–398 (1991).

Hamer, R.E. et al., "Production of transgenic rabbits, sheep and pigs by microinjection," *Nature*, 315:680–683 (1985).

Hanks, M. et al., "Rescue of the En–1 Mutant Phenotype by Replacement of En–1 with En–2," *Science*, 269:679–682 (1995).

Hoffman, C.S. et al., "A ten–minute DNA preparation from yeast efficiently releases autonomous plasmids for transformation of *Escherichia coli,*" *Gene*, 57:267–272 (1987).

Hogan et al. in *Manipulating the Mouse Embryo*: A Laboratory Manual, Cold Spring Harbor Laboratory Press, Cold Spring Harbor New York, pp. 91–149, 153–197, and 247–267 (1986).

Joyner, A.L. et al., "Production of a mutation in mouse En–2 gene by Homologous recombination in embryonic stem cells," *Nature*, 338:153–156 (1989).

Joyner, A.L. (ed.) in Gene Targeting: A Practical Approach, IRL Press, Oxford University Press, New York, pp. 107–144 and 1474–178 (1993).

Knudsen, C.M. et al., "Bax–Deficient Mice with Lymphoid Hyperplasia and Male Germ Cell Death," *Science*, 270:96–99 (1995).

Koller, B.H. et al., "Toward an animal model of cystic fibrosis: Targeted interruption of exon 10 of the cystic fibrosis transmembrane reglator gene in embryonic stem cells," *Proc. Natl. Acad. Sci.*, USA, 88:10730–10734 (1991).

Lorenz, M.C. et al., "Gene disruption with PCR products in *Saccharomyces cerevisiae,*" Gene, 158:113–117 (1995).

Luo, Y. et al., "A Novel Method for Monitoring *Mycobacterium bovis* BCG Trafficking with Recombinant BCG Expressing Green Fluorescent Protein." *Clinical Diagnostic Laboratory Immunlolgy*, 3 (6):761–768 (1996).

Lutz, C.T. et al., "Syrinx 2A: An improved λ phage vector designed for screening DNA libraries by recombination in vivo," *Proc. Natl. Acad. Sci.*, USA, 84:4379–4383 (1987).

Manivasakam, P. et al., "Micro–homology mediated PCR targeting in *Saccharomyces cerevisiae*, " *Nucleic Acids Research*, 23(14):2799–2800 (1995).

Marx, J., "Knocking Genes In Instead of Out," *Science*, 269:636 (1995).

Michaud, E.J. et al., "The embryonic lethality of homozygous lethal yellow mice ($A^y/A^y$) is associated with the disruption of a novel RNA–binding protein," *Genes & Development*, 7:1203–1213 (1993).

Miki, Y. et al., "A Strong Candidate for the Breast and Ovarian Cancer Susceptibility Gene BRCA1," *Science*, 266:66–71 (1994).

Mansour, S.L. et al., "Disruption of the proto–oncogene int–2 in mouse embryo–derived stem cells: a general strategy for targeting mutations to non–selectable genes," *Nature*, 336:348–352 (1988).

Moyer, J.H. et al., "Candidate Gene Associated with a Mutation Causing Recessive Polysystic Kidney Disease in Mice," *Science*, 264:1329–1333 (1994).

Oldenbburg, K.R. et al., "Recombination–mediated PCR–directed plasmid construction in vivo in yeast," *Nucleic Acids Research*, 25(2):451–452 (1997).

Orr–Weaver, T.L. et al., "Fungal Recombination, " *Microbiological Reviews*, 49(1):33–58 (1995).

Robertson, E.J. (ed.) in *Teratocarcinomas and embryonic stem cells, a practical approach*, IRL Press, Washington D.C., pp. 113–181 (1987).

Sambrook et al., *Molecular Cloning: A Laboratory Manual*, section pp. 1.19, 1.74–1.75, 2.6, 8.2–8.86, and 9.2–9.58 Cold Spring Harbor Laboratories (1989).

Seed, B., "Purification of genomic sequences from bacteriophage libraries by recombination and selection in vivo," *Nucleic Acids Research*, 11(8):2427–2445 (1983).

Sikorski, R.S. et al., "A System of Shuttle Vectors and Yeast Host Strains Designed for Efficient Manipulation of DNA in *Saccharomyces cerevisiae*, " *Genetics*, 122:19–27 (1989).

Silva, A.J. et al., "Deficient Hippocampal Long–Term Potentiation in α–Calcium–Calmodulin Kinase II Mutant Mice," *Science*, 257:201–206 (1992).

Snouwaert, J.N. et al., "An Animal Model for Cystic Fibrosis Made by Gene Targeting," *Science*, 257:1083–1088 (1992).

Soriano et al., "Targeted Disruption of the c–src Proto–Oncogene Leads to Osteopetrosis in Mice," *Cell*, 64:693–702 (1991).

Storck, T. et al., "Rapid construction in yeast of complex targeting vectors for gene maipulation in the mouse," *Nucleic Acids Research*, 24(22):4594–4596 (1996).

Tavtigian, S.V. et al., "The complete BRCA2 gene and mutations in chromosome 13q–linked kindreds," *Nature Genetics*, 12:333–337 (1996).

Thomas, K.R. et al., "Site–Directed Mutagenesis by Gene Targeting in Mouse Embryo–Derived Stem Cells," *Cells*, 51:503–512 (1987).

Travis, J. "Scoring a Technical Knockout in Mice," *Science*, 256:1392–1394 (1992).

Veis, D.J. et al., "Bcl–2–Deficient Mice Demostrate Fulminant Lymphoid Apoptosis, Polycystic Kidneys, and Hypopigmented Hair," *Cell*, 75:229–240 (1993).

Wang, N. et al., "Impaired Energy Homeostasis in C/EBPα Knockout Mice," *Science*, 269:1108–1112 (1995).

Zhang, Y. et al., "Positional cloning of the mouse obese gene and its human homologue," *Nature*, 372:425–432 (1994).

B. Eliceiri et al., "Stable integration and expression in mouse cells of yeast artificial chromosomes harboring human genes", *Proc. Natl. Acad. Sci.*, vol. 88: 2179–2183 (Mar. 1991).

I. Khrebtukova et al., "Utilization of microhomologous recombination in yeast to generate targeting constructs for mammalian genes",*Mutation Research–Fundamental and Molecular Mechanisms of Mutagenesis*, vol. 401, No. 1–2:11–25 (5 Jun. 1998).

International Search Report dated 25 Sep. 1998, International Appl. No. PCT/US98/11388.

```
CGGGGTGCGGAGCCGAGGGAAGCCGAGGAAGCGGTGCGGACTCTCGCGTGTG              60
CTCGGGCTCCTCACGCGGGCCCAGGCCGCCCTCTTCCCGCCCTCCGAGAGCAGAC          120
GCGCCCGTCGCCCTTCGGTGCCTGCCTTCCTCCAGACCCTCGGCCGGGTGAGCCCTAT       180
TTCTAGAGACAGCTGCTGACCCTGTAACT[CAAAGGACAAACTAGCTGG]TAAACTCA       240
TTCTTTGGTACTG[GTGAACACCATG]TCCTTGAAA[G]ATTCAGACCAGCAATGTAAC CAACAAG    300
                 M  S  L  K  I  Q  T  S  N  V  T  N  K          13
AATGACCCTAAGTCCATCAACTCTCGGGTCTTCATCGGAAATCTAAACACAGCTGTGGTG     360
 N  D  P  K  S  I  N  S  R  V  F  I  G  N  L  N  T  A  V  V     33
AAGAAGTCAGATGTGGAGACCATCTTTTCCAAGTACGGCCGAGTGGCTGGTGCTGTCTGTG    420
 K  K  S  D  V  E  T  I  F  S  K  Y  G  R  V  A  G  C  S  V     53
CACAAAGGCTATGCTTT[T]GTCCAGTATGCCAATGAGCGCCATGCCCGGGCCAGCTGTGCTG  480
 H  K  G  Y  A  F  V  Q  Y  A  N  E  R  H  A  R  A  A  V  L     73
GGAGAGAATGGGCGGGTAGCGGGCTAGGCTGGACAGACCCTGGACATCAACATGGCTGGAGAGCCC 540
 G  E  N  G  R  V  L  A  G  Q  T  L  D  I  N  M  A  G  E  P     93
AAGCCTAATAGAGACCCAAGGGCTAAAGAGAGCAGCAACTGCCATCTACAGGCTGTTTGAT    600
 K  P  N  R  P  K  G  L  K  R  A  A  T  A  I  Y  R  L  F  D    113
```

FIG. 8A

```
TATCGAGGCCGCCCTTTCTCCAGTGCCTGTGCCCAGGGCCAGTTCCGGTGAAGCGACCCGT    660
 Y  R  G  R  L  S  P  V  P  R  A  V  P  V  K  R  P  R           133

GTTACAGTCCCTTTGGTTCGCCGTGTCAAAACTACGATACCTGTTCAAGCTCTTTGCCCGC    720
 V  T  V  P  L  V  R  R  V  K  T  T  I  P  V  K  L  F  A  R    153

TCCACAGCTGTCACTACTGGCTCAGCCAAAATCAAGTTAAAGAGCAGTGAGCTACAGACC    780
 S  T  A  V  T  T  G  S  A  K  I  K  L  K  S  S  E  L  Q  T    173

ATCAAAACAGAGCTGACACAGATCAAGTCCAACATCGATGCCCTGTTGGGTCGCTTGGAA    840
 I  K  T  E  L  T  Q  I  K  S  N  I  D  A  L  L  G  R  L  E    193

CAGATTGCTGAGGAACAGAAGGCCAACCCAGATGGCAAGAAGAAGGGTGACAGCAGCAGT    900
 Q  I  A  E  E  Q  K  A  N  P  D  G  K  K  K  G  D  S  S  S    213

GGTGGAGGAGGAGGCAGCAGCAGTGGTGGAGGCGGCAGTAGCAATGTTGGTGGCAGCAGC    960
 G  G  G  G  S  S  S  G  G  G  G  S  S  N  V  G  G  S  S      233

GGCGGCAGCGGGAGCTGCAGCAGCAGCCGGCTACCAGCGCCCCAAGAAGACACGGCT      1020
 G  G  S  G  S  C  S  S  S  S  R  L  P  A  P  Q  E  D  T  A   253
```

FIG. 8B

```
TCTGAGGCAGGCACACCCCAAGGAGAAGTCCAAACTCGAGATGATGGTGATGAGGAGGGA    1080
 S  E  A  G  T  P  Q  G  E  V  Q  T  R  D  D  D  G  D  E  E  G   273

CTGCTAACACATAGCGAGGAGGAGCTGGAGCACAGCCAGGACACAGATGCAGAAGATGGA    1140
 L  L  T  H  S  E  E  E  L  E  H  S  Q  D  T  D  A  E  D  G     293

GCCTTGCAGTAAGCAGCTTAACAGGAGCATTGGCCACCAGCAGAAGGGCATCACTGTCTC    1200
 A  L  Q  *                                                      296

AGGGCCTCAAGGCCAGGCACCCATCTCTGGATGCCAGTCTATAGCGGGTACCAGAGGAAAGC    1260
TGGCAGCAGTAACTCTCTCCCCATGCATCCTAGCCAGTGAGTGCTACATCCTTTGCAAGT    1320
GGAGTTACTGGCCTACCCTTACCCCATGCATTCTTCCTGTCTGCACTGCCTGGGCCAAGG    1380
GGCAGAAACACTCTGCTCTTCCCCAGGACATTCCCAGGCTTGGGTTTTCTATAGG        1440
TTTGAAAGTAAAGGGGGAGGGGTGGGAAGGGTGGGAGGAACCTGACAATAAAGAGATTGG    1500
ATCCAAATAAAAAAAAA                                                1517
```

FIG. 8c

```
                        SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:1:

CAAATGATGG AAAATGTTCA TCTGGCACCA GAAACAGATG TTGGATCCTC TAGTACACTC        60

(2) INFORMATION FOR SEQ ID NO:2:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:2:

CTCAGTATCA TAGGCTGGGT TGTAGTCGTT GAAACCAGAG CTGCAGCTTT AAATAATCGG        60

(2) INFORMATION FOR SEQ ID NO:3:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:3:

CTCAGTATCA TAGGCTGGGT TGTAGTCGTT GAAACCAGAG CGCATCCCCA GCATGCCTGC        60

(2) INFORMATION FOR SEQ ID NO:4:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:4:
```

```
GTATAATTCA TTATGTGATA ATGCCAATCG CTAAG                              35
```

(2) INFORMATION FOR SEQ ID NO:5:

(i) SEQUENCE CHARACTERISTICS:
    (A) LENGTH: 35 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "primer"

(xi) SEQUENCE DESCRIPTION: SEQ ID NO:5:

```
TGAGGAAATT GCATCGCATT GTCTGAGTAG GTGTC                              35
```

(2) INFORMATION FOR SEQ ID NO:6:

(i) SEQUENCE CHARACTERISTICS:
    (A) LENGTH: 1517 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "primer"

(xi) SEQUENCE DESCRIPTION: SEQ ID NO:6:

```
CGGGGTGCGG AGCCGAGGGA AGCCGAGGGG GCGGAAGCGG TCGCGACTCT CGCGCGTGTG    60
CTCGGGCTCC TCACGCGGCG GCCAGGGCCG CCTCTTCCCT CCCGCCCTCC GAGAGCAGAC   120
GCGCCGTCGC CCTTCGGTGC CGCGCGGCTT CCTCCAGACC TCGGCGCGGG TGAGCCCTAT   180
TTCTAGAGAC AGCTGCTGCT GACCCTGTAA CTCAAAGGAC AAACTAGCTG GCTAAACTCA   240
TTCTTGGTAC TGGTGAACAC CATGTCCTTG AAGATTCAGA CCAGCAATGT AACCAACAAG   300
AATGACCCTA AGTCCATCAA CTCTCGGGTC TTCATCGGAA ATCTAAACAC AGCTGTGGTG   360
AAGAAGTCAG ATGTGGAGAC CATCTTTTCC AAGTACGGCC GAGTGGCTGG TTGCTCTGTG   420
CACAAAGGCT ATGCTTTTGT CCAGTATGCC AATGAGCGCC ATGCCCGGGC AGCTGTGCTG   480
GGAGAGAATG GGCGGGTGCT GGCTGGACAG ACCCTGGACA TCAACATGGC TGGAGAGCCC   540
AAGCCTAATA GACCCAAGGG GCTAAAGAGA GCAGCAACTG CCATCTACAG GCTGTTTGAT   600
TATCGAGGCC GCCTTTCTCC AGTGCCTGTG CCCAGGGCAG TTCCGGTGAA GCGACCCCGT   660
GTTACAGTCC CTTTGGTTCG CCGTGTCAAA ACTACGGATAC CTGTCAAGCT CTTTGCCCGC   720
TCCACAGCTG TCACTACTGG CTCAGCCAAA ATCAAGTTAA AGAGCAGTGA GCTACAGACC   780
ATCAAAACAG AGCTGACACA GATCAAGTCC AACATCGATG CCCTGTTGGG TCGCTTGGAA   840
CAGATTGCTG AGGAACAGAA GGCCAACCCA GATGGCAAGA AGAAGGGTGA CAGCAGCAGT   900
GGTGGAGGAG GAGGCAGCAG TGGTGGAGGC GGCAGTAGCA ATGTTGGTGG TGGCAGCAGC   960
GGCGGCAGCG GGAGCTGCAG CAGCAGCAGC CGGCTACCAG CGCCCCAAGA AGACACGGCT  1020
TCTGAGGCAG GCACACCCCA AGGAGAAGTC CAAACTCGAG ATGATGGTGA TGAGGAGGGA  1080
CTGCTAACAC ATAGCGAGGA GGAGCTGGAG CACAGCCAGG ACACAGATGC AGAAGATGGA  1140
GCCTTGCAGT AAGCAGCTTA ACAGGAGCAT TGGCCACCAG CAGAAGGGCA TCACTGTCTC  1200
AGGCCTCAAG CCAGGCACCC ATCTCTGGAT GCCAGTCTAT AGCGGGTACC AGAGGAAAGC  1260
TGGCAGCAGT AACTCTCTCC CCATGCATCC TAGCCAGTGA GTGCTACATC CTTTGCAAGT  1320
GGAGTTACTG GCCTACCCTT ACCCCATGCA TTCTTCCTGT CTGCACTGCC TGGGCCAAGG  1380
GGCAGAAACA CTCTGCTCTT CTTCCCCAGG ACATTCCCAG GCTTGGGGTT TTTCTATAGG  1440
```

```
TTTGAAAGTA AAGGGGGGAG GGTGGGAAGG GTGGGAGGAA CCTGACAATA AAGAGATTGG    1500

ATCCAAATAA AAAAAAA                                                  1517

(2) INFORMATION FOR SEQ ID NO:7:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:7:

TGAACACCAT GTCCTTGAAG ATTCAGACCA GCAATGTAAC TTGGATCCTC TAGTACACTC    60

T                                                                   61

(2) INFORMATION FOR SEQ ID NO:8:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:8:

GCTCATTGGC ATACTGGACA AAAGCATAGC CTTTGTGCAC CGCATCCCCA GCATGCCTGC    60

T                                                                   61
```

EFFICIENT CONSTRUCTION OF GENE TARGETING VECTORS

BACKGROUND OF THE INVENTION

One of the most useful approaches for studying the functions of specific genes (including their health related functions) is to examine the effects of mutations within those genes (i.e., the phenotype of the mutation). This approach involves correlating mutations within specific genes with the phenotypes or disease conditions that result from those mutations. This has been particularly fruitful in recent years with the identification of genes for such diseases as cystic fibrosis (Snouwaert et al., *Science*, 257:1083 (1992)), obesity (Zhang et al, *Nature*, 372: 425 (1994)), polycystic kidney disease (Moyer et al., *Science*, 264:1329 (1994)), breast cancer [Miki et al., *Science*, 266:66–71 (1994); Tavtigian et al., *Nat. Genet.*, 12:333–337 (1996)], and other diseases. In these cases, the function of the implicated genes was not apparent solely from their DNA sequence but rather was defined by a disease condition associated with mutations in the genes.

A particularly productive approach to understanding the function of a particular gene in animals involves the disruption of the gene's function which is colloquially referred to as a "targeted mutagenesis". One common form of targeted mutagenesis is to generate "gene knockouts". Typically, a gene knockout involves disrupting a gene in the germline of an animal at an early embryonic stage. (See, Thomas et al., *Cell*, 51:503 (1987).) Once established in the germline, it is possible to determine the effect of the mutation on the animal in both the heterozygous and homozygous states by appropriate breeding of mice having the germline mutation.

Among the many examples of the use of knockout technology utilized to investigate gene function are U.S. Pat. Nos. 5,625,122 and 5,530,178 to Mak, T. which describe the production of mice having a disrupted gene encoding lymphocyte-specific tyrosine kinase $p56^{lck}$ and Lyt-2, respectively. Silva et al., *Science*, 257:201 (1992) produced mice having a disrupted α-Calcium Calmodulin kinase II gene (αCaMKII gene) which resulted in animals having an abnormal fear response and aggressive behavior. (See, also, Chen et al., *Science*, 266:291 [1994]). Wang et al., *Science*, 269:1108 (1995) demonstrated that the disruption in mice of the C/EPBα gene which encodes a basic leucine zipper transcription factor results in impaired energy homeostasis in the mutant animals. Knudsen et al., *Science*, 270:960 (1995) demonstrated that disruption of the BAX gene in mice results in lymphoid hyperplasia and male germ cell death.

The most common approach to producing knockout animals involves the disruption of a target gene by inserting into the target gene (usually in embryonic stem cells), via homologous recombination, a DNA construct encoding a selectable marker gene flanked by DNA sequences homologous to part of the target gene. When properly designed, the DNA construct effectively integrates into and disrupts the targeted gene thereby preventing expression of an active gene product encoded by that gene.

Homologous recombination involves recombination between two genetic elements (either extrachromosomally, intrachromosomally, or between an extrachromosomal element and a chromosomal locus) via homologous DNA sequences, which results in the physical exchange of DNA between the genetic element. Homologous recombination is not limited to mammalian cells but also occurs in bacterial cells, yeast cells, in the slime mold *Dictyostelium discoideum* and in other organisms. For a review of homologous recombination in mammalian cells, see Bollag et al., *Ann. Rev. Genet.*, 23:199–225 (1989) (incorporated herein by reference). For a review of homologous recombination in fungal cells, see Orr-Weaver et al., Microbiol. Reviews, 49:33–58 (1985) incorporated herein by reference.

As is illustrated by the foregoing, gene knockout technology has often been used in mice and has allowed the identification of the function of numerous genes and, in some cases, ascertainment of their roles in disease. Much may be learned about the function of human genes from studies of mouse genetics because the vast majority of genes in humans have homologous counterparts in the mouse. Because of this high level of homology between the species, it is now possible to define the function of individual human genes and to elucidate their roles in health and disease by making targeted germline mutations in selected genes in the mouse. The phenotype of the resulting mutant mice can be used to help define the phenotype in humans.

With the increasing awareness that mouse mutations can provide such useful insights about the function of genes from humans, a great deal of interest is developing to systematically generate mutations within genes in mice that correspond to those genes which are being isolated and characterized as part of various genome initiatives such as the Human Genome Project. The problem with utilizing these procedures for large-scale mutagenesis experiments is that the technologies for generating transgenic animals and targeted mutations are currently very tedious, expensive, and labor intensive.

One of the biggest problems with the efficient generation of targeted mutations is the generation of the targeting construct. Targeting constructs are typically prepared by isolating genomic clones containing the region of interest, developing restriction maps, frequently engineering restriction sites into the clones, and manually cutting and pasting fragments to engineer the construct. See, e.g., Mak, T. U.S. Pat. Nos. 5,625,122 and 5,530,178; Joyner et al., *Nature*, 338:153–156 (1989); Thomas et al., supra; Silva et al., supra, Chen et al., supra; Wang et al., supra; and Knudsen et al., supra. This process can take a single highly skilled individual at least several weeks, often several months, to complete. Thus, in order to more rapidly and efficiently elucidate the functions of a variety of genes and to understand their role in health and disease, there exists a need to develop more efficient methods for the production of targeting constructs which do not require detailed restriction mapping and certain other complex molecular engineering steps.

SUMMARY OF THE INVENTION

The invention is directed to highly efficient methods for preparing gene targeting vectors by exploiting the ability of certain cells to mediate homologous recombination. The invention is also directed to targeting constructs made by or obtainable by the methods of the invention.

The targeting constructs produced by the methods of the invention may be designed for either "knocking out" genes (or regulatory sequences thereof) or for "knocking in" genes into preselected genetic loci. Gene regulatory elements such as promoters or other transcriptional regulatory elements may also be "knocked in" in proximity to a target gene so as to modulate expression of the target gene.

Targeting constructs according to the present invention comprise targeting DNA sequences which are homologous to one or more portions of a gene or genetic locus to be targeted. Targeting constructs may further comprise disruptor elements (such as marker genes) flanked by the targeting DNA sequences which when introduced into the targeted gene or locus (hereinafter the "target") by way of homologous recombination, disrupts the expression of the targeted gene. Alternatively, instead of a disruptor element, a transcriptional regulatory sequence or another gene or portion thereof may be flanked by homologous targeting sequences, thereby allowing their introduction into a gene or genetic locus. Such alternative constructs may also comprise a marker gene in an orientation that allows its expression but does not disrupt the function of the target gene.

Targeting constructs may also comprise replication competent or deficient vectors such as plasmids, phagemids, cosmids, artificial yeast chromosomes, and viruses such as bacteriophage or mammalian viruses. The use of replication incompetent vectors may require the coincident use of helper viruses or other helper elements which complement the replication defect in the vector.

Cells preferred as hosts for the practice of the invention include those cells competent to mediate homologous recombination, that is cells that permit recombination between homologous DNA sequences on the same genetic element or between separate genetic elements. Preferred cells include fungi including yeast, mammalian cells, insect cells, slime mold (e.g. *Dictyostelium discoideum*) and bacterial cells. Most preferred are yeast cells and, in particular, *Saccharomyces cerevisiae*.

A preferred method for preparing gene targeting vectors in yeast by homologous recombination according to the present invention comprises:

a) preparing a shuttle vector comprising a yeast selectable marker, a bacterial selectable marker and a fragment of genomic DNA corresponding to at least part of a functional component of a genomic sequence to be targeted;

b) preparing a specific engineered fragment (SEF) comprising a marker cassette, the marker cassette comprising a second yeast selectable marker different from the yeast selectable marker of step a), and a selectable marker capable of expression in mammalian embryonic stem cells said marker cassette being flanked on each side by mammalian gene-specific flanking sequences (targeting sequences) homologous to a portion of the gene to be targeted;

c) transforming yeast cells with the shuttle vector of step a) and with the SEF of step b), and allowing said shuttle vector and said SEF to recombine by homologous recombination;

d) selecting the transformed yeast cells for expression of the yeast selectable markers; and e) isolating the targeting vector produced by recombination between the shuttle vector and the SEF from the yeast cells selected in step d).

Preferably, the mammalian gene-specific flanking sequences comprising the SEF each comprise at least 20 base pairs (bp) of DNA. More preferably, the gene-specific flanking sequences each comprise from at least 40 bp of DNA. The SEF may also comprise a selectable marker cassette comprising a selectable marker flanked by targeting sequences. The marker sequence may also serve as a disrupter sequence which, along with expressing a protein which allows selection of clones containing the marker, can serve to prevent expression of an active gene product encoded by the targeted gene.

Alternatively, the SEF may comprise a transcription regulatory sequence or all or part of another gene flanked by targeting sequences. In a preferred embodiment a selectable marker cassette may further comprise a transcriptional regulatory sequence located 3' to the selectable marker sequence so as to allow selection of the recombinant targeting vector while allowing the transcriptional regulatory sequence to become operably linked to a targeted gene to which it is directed. Preferably, a transcription termination sequence is located between the selectable marker sequence and the transcriptional regulatory element so as to prevent transcriptional read through from the marker and through the transcriptional regulatory sequence.

The fragment of genomic DNA (corresponding to a genomic region to be targeted) used in the practice of the present invention comprises from about one kilobase (kb) to about 15 kb and contains at least part of the gene sequence to be targeted. Preferably, the genomic fragment is greater than 6 kb. Preferably, the fragment of genomic DNA comprises from about 0.5 to about 5 kb of DNA on each side of the specific site being targeted in the target gene.

The first and second yeast selectable markers according to the present invention are selected from the group consisting of His3, Ura3, and Leu2, although other markers effective for selection of yeast expressing the markers are well known in the art. Preferably, the first yeast selectable marker found in the shuttle vector and the SEF are different from one another.

Preferred bacterial selectable markers according to the invention are selected from the group consisting of tet$^r$, amp$^r$, chloramphenol resistance and others well known in the art.

Suitable mammalian cell selectable markers may be biochemical markers which permit growth of the mammalian cells in selective medium and may be selected from the group consisting of neo$^r$, hygromycin resistance marker, Salmonella his D, puromycin N-acetyl-transferase, and other markers well known in the art. Other suitable mammalian cell markers may be physical markers, such as the green fluorescent protein, luciferase or other markers, the expression of which may be detected by physical means such as by fluorescence or color production. (See, e.g., Chalfie et al., *Science*, 263:802–805 [1994].)

Markers which allow physical selection provide the added benefit of facilitating the automation of the methods of the present invention thereby providing even greater throughput in the production of targeting constructs.

In another embodiment of the invention, the second yeast selectable marker and mammalian cell selectable marker are the same marker, which functions for selection in both mammalian cells and in yeast.

Still another aspect of the invention is directed to targeting constructs made by or obtainable by using the methods of the invention.

The invention is also directed to methods for preparing a gene targeting construct, the method comprising culturing homologous recombination competent cells containing a specific engineered fragment (SEF) and a shuttle vector, allowing the SEF to recombine via homologous sequences and isolating the resulting targeting vector.

Still another aspect of the invention is a method for preparing a gene targeting construct in homologous recombination competent yeast cells, the method comprising the steps of preparing a first DNA construct comprising all or part of a gene to be targeted; preparing a second DNA construct comprising a DNA for insertion into the targeted gene, the DNA for insertion being flanked on both sides by gene specific sequences homologous to a portion of the targeted gene; introducing the first and second constructs into homologous recombination competent cells,; allowing the first and second DNA constructs to recombine via their homologous sequences thereby producing a targeting construct; and isolating the targeting construct.

Also contemplated by the present invention are transgenic animals or those containing a targeted mutation produced using the targeting vectors of the present invention.

BRIEF DESCRIPTION OF THE DRAWINGS

FIGS. 8A–C depicts the cDNA sequence of the Raly locus.

DETAILED DESCRIPTION

Figure 1:
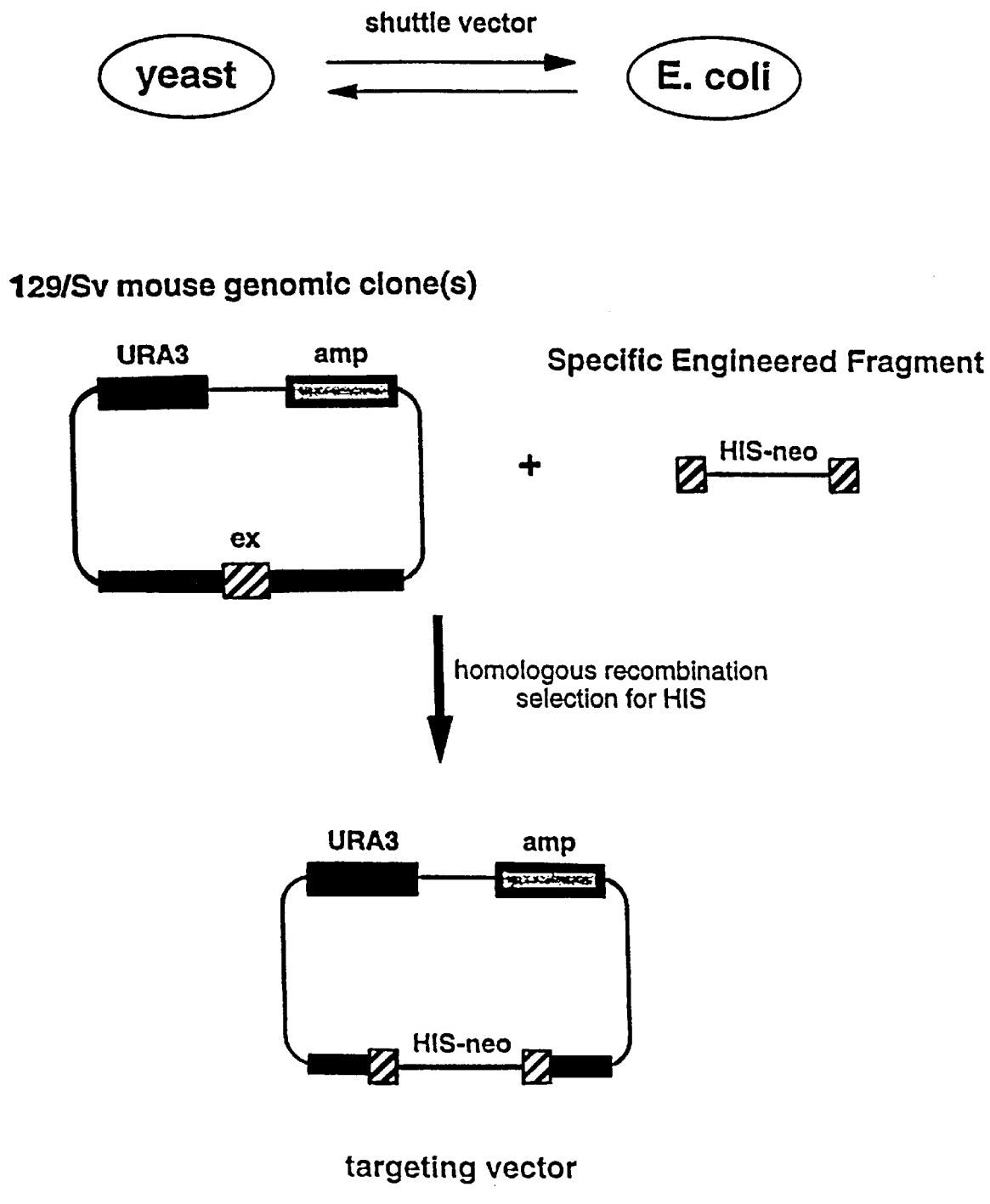
FIG. 1 depicts a scheme for utilizing homologous recombination in yeast to generate targeting constructs.

In one of its aspects, the present invention is directed to methods for producing targeting constructs for the purpose of introducing into the genome of an animal, a disruption at a particular genetic locus (i.e., a targeted mutation). The targeting constructs of the present invention may also be used to introduce into a genomic locus another functional gene ("knock in") or to otherwise alter the function or expression of a gene, for example, by knocking in a foreign promoter so as to place it in operative linkage with a gene in a chromosomal locus. The targeting construct is inserted into the appropriate genome location by taking advantage of the cell's ability to mediate homologous recombination between homologous sequences in the targeting construct and the sequences in the genomic locus or gene of interest.

Unlike traditional methods for constructing targeting vectors, the practice of the present invention does not require detailed restriction maps or extensive DNA sequence information in order to prepare targeting vectors. Because such detailed information is not required to prepare targeting constructs according to the present invention, vectors may be produced more quickly and effectively than previously employed methods.

Targeted mutagenesis of a gene refers to an alteration (e.g., partial or complete inactivation) of normal production or structure of the polypeptide encoded by the targeted gene of a single cell, selected cells or all of the cells of an animal (or in culture) by introducing an appropriate targeting construct into a site in the gene to be disrupted.

Targeted mutagenesis may also refer to "knocking in" a gene which means replacing one gene with all or part of another gene for the purpose of determining, for example, whether two genes are functionally equivalent (see, e.g., Hanks et al., Science, 269:679 (1995), incorporated herein by reference), although other applications are possible. For example, transcriptional regulatory sequences such as promoters may be knocked in to a region of a genome so as to be operatively linked to a structural sequence.

In most cases, targeting constructs are constructed so as to include at least a portion of a gene to be disrupted. Typically, the portion of the gene included in the targeting construct is interrupted by insertion of a marker sequence (usually a selectable marker) that disrupts the reading frame of the interrupted gene so as to preclude expression of an active gene product. This most often causes a knock out or inactivation of a gene. An exemplary selectable marker is the $neo^r$ gene (under the control of a promoter that functions in cells into which the marker is introduced, e.g., the phosphoglycerate kinase promoter (PGK) which confers on cells expressing the gene resistance to the antibiotic G418).

Prior to the present invention, the preparation of such constructs typically involved restriction mapping in order to identify convenient restriction sites in the gene fragment to be used to "cut and paste" DNA fragments to ultimately generate a targeting vector. However, mapping frequently reveals that convenient restriction sites are not available and therefore, they must be engineered into various components of the targeting constructs. According to the present invention, detailed mapping and sequence information are not required in order to prepare targeting constructs which results in a significant saving of time and effort in preparing targeting constructs.

When such targeting constructs are introduced into embryonic stem cells, they can recombine with the target gene in the cell via the homologous sequences in both the construct and in the genomic region to be disrupted. The result of the homologous recombination event is often the insertion of the marker sequence into the targeted gene, thereby disrupting the gene. Similarly, targeting constructs designed for knocking in genes can recombine at the homologous genomic site by homologous recombination and will result in the introduction of all or a portion of a gene into that locus. Techniques for knocking in genes are described in detail in Hanks et al., Science, 269:679 (1995) which is incorporated herein by reference.

In order to introduce the targeting construct into the germline of an animal, the targeting construct is first introduced into an undifferentiated totipotent cell termed an embryonic stem (ES) cell wherein the construct can recombine with the selected genomic region via their homologous sequences. ES cells are derived from an embryo or blastocyst of the same species as the developing embryo into which they are to be introduced. ES cells are typically selected for their ability to integrate into the inner cell mass and contribute to the germ line of an individual when introduced into the mammal in an embryo at the blastocyst stage of development. Thus, any ES cell line having this capability is suitable for use in the practice of the present invention.

The cells are cultured and prepared for introduction of the targeting construct using methods well known to the skilled artisan. (See, e.g., Robertson, E. J. ed. "Teratocarcinomas and Embryonic Stem Cells, a Practical Approach", IRL Press, Washington D.C. [1987]; Bradley et al., *Current Topics in Devel. Biol.* 20:357–371 [1986]; by Hogan et al. in "Manipulating the Mouse Embryo": A Laboratory Manual, Cold Spring Harbor Laboratory Press, Cold Spring Harbor N.Y. [1986]; Thomas et al., *Cell*, 51:503 [1987]; Koller et al., *Proc. Natl. Acad. Sci. USA*, 88:10730 [1991]; Dorin et al., *Transgenic Res.*, 1:101 [1992]; and Veis et al., *Cell*, 75:229 [1993] all of which are incorporated herein by reference). The targeting construct may be introduced into ES cells by any one of several methods known in the art including electroporation, calcium phosphate co-precipitation, retroviral infection, microinjection, lipofection and other methods. Insertion of the targeting construct into the targeted gene is typically detected by selecting cells for expression of the marker gene contained in the targeting construct which is typically under the control of a promoter which is functional in the target cell type (i.e., promoters which function in embryonic stem cells). ES cells expressing the marker sequence are then isolated and expanded.

The ES cells having the disruption are then introduced into an early-stage mouse embryo (e.g., blastocyst) (see, e.g., Robertson, supra, Bradley, supra, and Monsour et al., *Nature*, 336:348 (1988)) incorporated herein by reference. Blastocysts and other early stage embryos used for this purpose are obtained by flushing the uterus of pregnant animals for example, by the methods described in Robertson et al., supra and Bradley et al., supra. The suitable stage of development for the blastocyst is species dependent, however, for mice it is about 3.5 days post-fertilization.

While any embryo of the right age/stage of development is suitable for implantation of the modified ES cell, preferred most embryos are male and have genes coding for a coat color or other phenotypic marker that is different from the coat color or other phenotypic marker encoded by the ES cell genes. In this way, the offspring can be screened easily for the presence of the targeted mutation by looking for mosaic coat color (e.g. agouti) or the other phenotypic markers (indicating that the ES cell was incorporated into the developing embryo). Thus, for example, if the ES cell line carries the genes for white fur, the host embryos selected will preferably carry genes for black or agouti fur.

An alternate method of preparing an embryo containing ES cells that possess the targeting construct is to generate "aggregation chimeras". A morula of the proper developmental stage (about 2½ days post-fertilization for mice) is isolated. The zona pellucida can be removed by treating the morula with a solution of mild acid for about 30 seconds, thereby exposing the "clump" of cells that comprise the morula. Certain types of ES cells such as the R1 cell line for mice can then be co-cultured with the morula cells, forming an aggregation chimera embryo of morula and ES cells, (Joyner, A. L., "Gene Targeting", *The Practical Approach Series*, JRL Press Oxford University Press, New York, 1993, incorporated herein by reference).

A refinement of the aggregation chimera embryo method can be used to generate an embryo comprised of essentially only those ES cells containing the knockout construct. In this technique, a very early stage zygote (e.g., a two-cell stage zygote for mice) is given a mild electric shock. This shock serves to fuse the nuclei of the cells in the zygote thereby generating a single nucleus that has two-fold (or more) the DNA of a naturally occurring zygote of the same developmental stage. These zygotic cells are excluded from the developing embryo proper, and contribute only to forming accessory embryonic structures such as the extraembryonic membrane. Therefore, when ES cells are co-cultured with the zygotic cells, the developing embryo is comprised exclusively of ES cells, (see Joyner, A. L., supra).

After the ES cells have been incorporated into the aggregation chimera or into the blastocyst, the embryos may be implanted into the uterus of a pseudopregnant foster mother. While any foster mother may be used, preferred foster mothers are typically selected for their ability to breed and reproduce well, and for their ability to care for their young. Such foster mothers are typically prepared by mating with vasectomized males of the same species. The pseudopregnant stage of the foster mother is important for successful implantation, and it is species dependent. For mice, this stage is about 2–3 days of pseudopregnancy.

Offspring that are born to the foster mother may be screened initially for mosaic coat color or another phenotypic marker (where the phenotype selection strategy has been employed). In addition, or as an alternative, chromosomal DNA obtained from tail tissue of the offspring may be screened for the presence of the targeted mutation using Southern blots and/or PCR. The offspring that are positive for homologous recombination at the targeted locus will typically be a mosaic of wild-type cells derived from the host embryo and heterozygous cells derived from injected ES cells (i.e., chimeric offspring). Chimeric offspring are crossed with wild-type partners to generate offspring that are heterozygous for the targeted mutations, i.e., all of their cells are heterozygous for the mutation.

Methods for producing transgenic mammals, including rabbits, pigs, and rats, using micro-injection are described in Hamer et al., *Nature* 315:680–683 (1985).

If animals homozygous for the targeted mutation are desired, they can be prepared by crossing animals heterozygous for the targeted mutation. Mammals homozygous for the disruption may be identified by Southern blotting of equivalent amounts of genomic DNA from mammals that are the product of this cross, as well as mammals of the same species that are known heterozygotes, and wild-type mammals. Alternatively, specific restriction fragment length polymorphisms can be detected which co-segregate with the mutant locus. Probes to screen the Southern blots for the presence of the targeting construct in the genomic DNA can be designed as described below.

Other means of identifying and characterizing the offspring having a disrupted gene are also available. For example, Northern blots can be used to probe mRNA obtained from various tissues of the offspring for the presence or absence of transcripts. Differences in the length of the transcripts encoded by the targeted gene can also be detected. In addition, Western blots can be used to assess the level of expression of the targeted gene by probing the Western blot with an antibody against the protein encoded by the targeted gene. Protein for the Western blot may be isolated from tissues where this gene is normally expressed. Finally, in situ analysis (such as fixing the cells and labeling with antibody or nucleic acid probe) and/or FACS (fluorescence activated cell sorting) analysis of various cells from the offspring can be conducted using suitable antibodies to look for the presence or absence of the gene product.

While the foregoing discussion describes the use of targeting constructs to introduce DNA into a genomic locus via homologous recombination, the process of homologous recombination may also, according to the present invention, be used to prepare the targeting constructs themselves.

In general, the method of the present invention involves preparing at least two DNA constructs, a shuttle vector, and a specifically engineered fragment (SEF). A shuttle vector according to the present invention comprises a yeast selectable marker, a bacterial selectable marker and a fragment of genomic DNA corresponding to a portion of the genomic site to be targeted. The fragment preferably corresponds to all or part of an exon. Alternatively, the fragment of genomic DNA may correspond to a portion of the 5' or 3' non-coding region of a gene or all or a portion of an intron.

A specific engineered fragment comprises unique flanking sequences (targeting sequences) different from one another and which correspond to sequences in the genomic site to be targeted. Interposed between the flanking sequences of the SEF may be a marker sequence which may serve as both a marker and a disruption sequence. Alternatively, a transcriptional regulatory sequence or a combination of a marker sequence disposed 5' to a transcriptional regulatory sequence may be interposed between the flanking sequences. The shuttle vector and the SEF are introduced into yeast cells which mediate recombination between the homologous sequences in the shuttle vector and the SEF, effectively introducing the DNA interposed between the unique flanking DNA into the fragment of genomic DNA in the shuttle vector. The resulting targeting construct may be used, as described above, to produce targeted mutations.

It should be noted that the DNA sequences involved in homologous recombination according to any aspect of the present invention need not be 100% homologous with one another (or identical), however in general, the greater the homology between sequences the greater the efficiency of recombination.

The yeast *Saccharomyces cerevisiae* has highly developed genetic systems involving homologous recombination that have been very useful for genetic engineering in vivo (see, e.g., Orr-Weaver et al., *Microbiol. Rev.*, 49:33 [1985]). In yeast, linear double-stranded (ds) DNA undergoes efficient homologous recombination with either chromosomal or plasmid targets (Orr-Weaver et al., supra), which is in contrast to the fate of linear ds DNA in wild-type *E. coli* which, when introduced into the bacterial cell, is degraded. The present invention is directed to exploiting the yeast homologous recombination system in order to increase the efficiency of production of targeting constructs for the generation of targeted mutations (e.g., knock out or knock in mutations).

According to the present invention, homologous recombination in yeast allows the preparation of targeting constructs to target essentially any segment of the mouse or other mammalian genome. Unlike the traditional methods used to make targeting constructs, the methods of the present invention do not require detailed restriction mapping, convenient restriction sites, nor the engineering of restriction sites, but requires sequence of at least a portion of a cDNA and a genomic clone comprising at least a part of an exon of a target gene or a portion of the locus to be targeted (including 5' or 3' untranslated sequences or intron sequences) and limited sequence information regarding the exon or locus. The approach is exemplified below with reference to particular genes and particular mouse strains, however, the methods of the present invention are readily adaptable to other genes and other species of mice and other mammals. The general method of the invention is depicted schematically in FIG. 1.

By way of overview, a fragment of mouse 129/Sv (see, e.g., Knudsen et al., *Science*, 270:96 (1995)) genomic DNA obtained from a genomic library of 129/sv DNA containing at least part of the gene to be targeted is cloned into a yeast/*E. coli* shuttle vector which has selectable markers allowing selection in yeast and in *E. coli*, (e.g., URA3 [yeast] and amp$^r$ [*E. coli*] selectable markers). Methods for preparing genomic libraries and cDNA libraries are well known in the art and are described in Sambrook et al., Molecular Cloning, A Laboratory Manual, (section 9, pp. 9.2–9.58 and section 8, pp. 8.2–8.79, respectively) Cold Spring Harbor N.Y. (1989) and in Current Protocols in Molecular Biology, (section 5, pages 5.0.1–5.11.2) Ausubel et al., Eds. John Wiley and Sons Inc. (1987), the relevant sections of which are incorporated herein by reference. The shuttle vector into which the genomic DNA has been cloned is capable of propagation in both yeast cells in which it will serve as a target for recombination and generation of the targeting vector and is capable of propagation and amplification in *E. coli* and from which significant amounts of the vector may be obtained.

At the same time, a specific engineered fragment (SEF) is generated by the polymerase chain reaction (PCR). The SEF may contain markers for selection in yeast (e.g., HIS3) and in ES cells (e.g., PGK-neo, neomycin resistance gene under the control of a promoter capable of directing expression of the neo gene in ES cells) (i.e., the His-neo segment) (marker cassette) flanked on each side by about 40 base pairs (bp) of unique sequences (prepared by the polymerase chain reaction or synthetically) corresponding to the region of the gene to be disrupted and through which homologous recombination will occur. The selection of DNA sequence for use as unique flanking sequences may be made based on the cDNA sequence of the gene or locus to be targeted or the genomic sequence but does not require the presence of known restriction sites nor does it require that restriction sites be engineered into the unique genomic DNA. The SEF may also comprise a single marker sequence which allows selection in both yeast and ES cells. The length of the unique flanking sequences may vary from about 10 to 200 bp or more. Preferred lengths are from about 40 to about 200 bp although longer sequences may increase the efficiency of recombination. Lengths of 1 kb may be advantageous to the efficiency of homologous recombination.

Other exemplary selectable markers include genes conferring resistance to hygromycin, genes encoding the Salmonella his D gene (which allows a cell to convert histidinal to histidine), puromycin D-acetyl transferase and others. The markers used are not limited to those disclosed above but also include a variety of other selectable markers well known in the art and which are useful for selection in yeast, *E. coli*, and/or mammalian cells.

The shuttle vector comprising all or part of the genomic region to be targeted and the SEF are introduced into a yeast strain, e.g., the D1500 of *Saccharomyces cerevisiae* by lithium acetate transformation or by electroporation (or by other methods known in the art) either sequentially or simultaneously. Once in the yeast cell, the SEF and the shuttle vector can recombine by homologous recombination via their homologous gene sequences (i.e., the flanking sequences of the SEF and the genomic sequence in the shuttle vector), thereby inserting into the homologous DNA of the shuttle vector the marker or markers from the SEF thereby generating a targeting construct. The targeting construct sequences will contain integrated HIS3-neo genes (or whatever markers were used in construction of the SEF) flanked by sequences of the targeted gene and may be identified by selecting for the HIS3 marker by growing yeast containing the construct in medium lacking histidine. Media for selection of other markers are also known in the art (supra). Targeted clones are then identified by determining whether HIS3 and the plasmid URA3 marker cosegregate by replica plating transformants on medium-lacking uracil.

To confirm that the integration of the SEF occurred by homologous recombination, targeted plasmids are then analyzed by PCR using a primer from each side of the insertion. Finally, the targeting vector containing the insertion is shuttled into bacteria so that adequate quantities of purified construct (e.g., plasmid) DNA can be prepared for final analysis and introduction into ES cells. In this way, targeting vectors can be generated with considerable ease and speed, obviating the extensive gene mapping and the search for suitable restriction sites required by traditional methods. It should be noted that the ease of construction and selection of targeting vectors according to the methods of the present invention readily lends itself to automated procedures, particularly when certain physically detectable (e.g., colorimetric, fluorometric, and others) markers are used for selection of the targeting vector.

The present invention is described in more detail with reference to the following non-limiting examples.

Example 1 describes the generation of targeting vectors in yeast by homologous recombination as exemplified by the use of the Tg737 gene.

Example 2 describes the construction of a His-neo SEF.

Example 3 describes the introduction of targeting constructs into ES cells.

Example 4 describes methods for the detection of homologous recombination in ES cells by long range PCR.

Example 5 describes the production of Tg737 knockout mice.

Example 6 describes the generation of a targeting vector for the Raly gene.

EXAMPLE 1

Generation of Targeting Vectors by Homologous Recombination in Yeast

Although the methods of the present invention do not require detailed restriction maps and intron exon structure and information, the methods were tested using a gene with a known restriction map and exon/intron structure as a proof of principle. The Tg737 gene selected for use in the method was identified by Moyer et al., *Science* 264:1329–1333, 1994 (incorporated herein by reference) and has been characterized by restriction mapping and partial sequencing.

Figure 2:
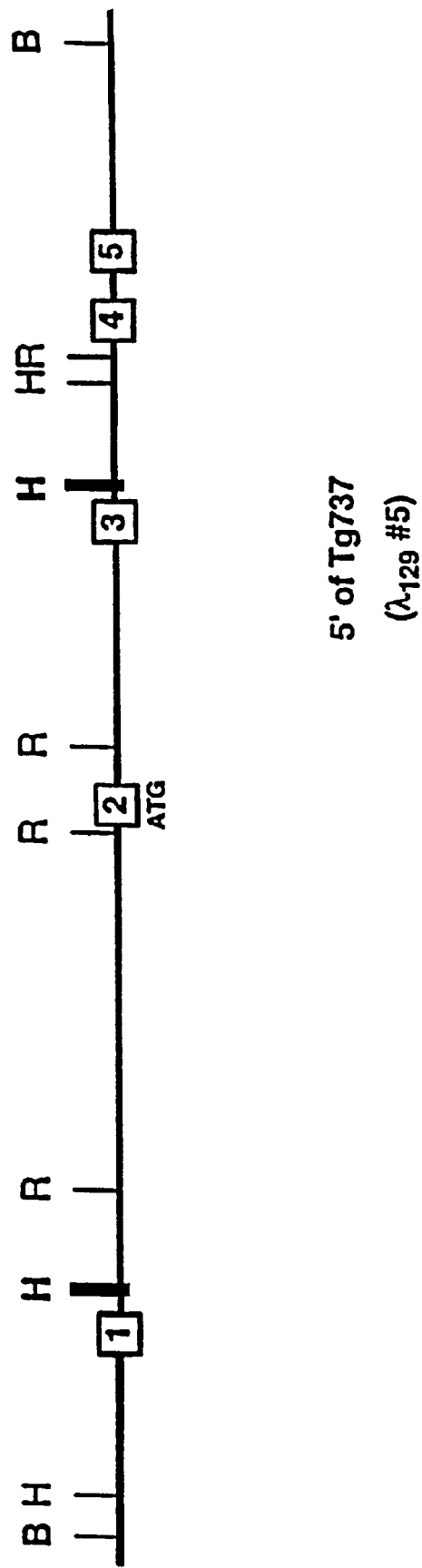
FIG. 2 depicts the restriction map and intron-structure exon of the Tg737 gene.

A restriction map of the 5'-region of the Tg737 is shown in FIG. 2. The 10.5 kb HindIII fragment containing exon 2 (with the ATG translation initiation codon) was subcloned from a 129/Sv mouse genomic clone in λ Dash II (Stratagene, La Jolla, Calif.) into the *E. coli*/yeast shuttle vectors pRS416 and pRS426, respectively. (Sikorski et al., *Genetics*, 122:19–27 (1989); Christian et al., *Gene*, 110:119–122, both incorporated herein by reference), although other shuttle vectors may be used. The shuttle vector pRS416 is a low-copy-number centromere-based plasmid (YCp), while pRS426 is a multicopy 2μ circle-based plasmid (YEp). Both vectors are derived from pBluescript (Stratagene) and have URA3 (yeast) and amp$^r$ (*E. coli*) selectable markers. Although a 10.5 kb fragment of Tg737 genomic DNA was used in this case, other sequence lengths may be used for subcloning into the shuttle vector. Preferred lengths are 6 kilobases (kb) or more. In one preferred embodiment the genomic fragment has 1 kb or more of sequences flanking each side of the exon (or locus) to be targeted although shorter flanking sequences may be used.

At the same time, a specific engineered fragment (SEF) (Tg737-HIS-SEF) was generated by PCR using hybrid 60–61-mer primers. A typical SEF contains markers for a selection in yeast (his 3 gene) and in ES cells (neo$^r$ gene) flanked on each side by 40 bp of unique sequence corresponding to the 5' and 3' termini of the genomic region to be disrupted. More particularly, Tg737-HIS SEF (HIS3 gene sequence flanked on both sides by 40 bp of the Tg737 exon 2 sequences) was produced using the following forward and reverse primers (sequence from the his cassette is given in bold):

```
                                        (SEQ ID NO: 1)
forward primer (RW 641):
CAAATGATGGAAAATGTTCATCTGGCACCAGAAACAGATGT
```
TGGATCCTCTAGTACACTC

```
                                        (SEQ ID NO: 2)
reverse primer (RW 642):
CTCAGTATCATAGGCTGGGTTGTAGTCGTTGAAACCAGAGC
```
TGCAGCTTTAAATAATCGG

Appropriate PCR conditions are readily determined although typical conditions for purposes of the present example are as follows: total volume 50 μl with 25 pmoles of each primer, 10 μg plasmid, Fisher Taq polymerase, cycling at 94° C. for 5 minutes; 30× (95° C. for 30 seconds; 55° C. for 1 minute; 72° C. for 2 minutes) and 72° C. for 10 minutes in an MJ Research thermocycler.

It should be noted that the homology between the exon sequences of the SEF and the exon (or locus) sequences in the shuttle vector need not be perfect (100%) although between 80% to 100% homology is preferred. (See, Bollag et al., supra for a discussion of the effects of divergent sequences on the efficiency of recombination in mammalian cells and Seed, *Nucl. Acids Res.*, 11:2427 (1983) for a similar discussion regarding bacteria.)

The SEF generated in this case consisted of the HIS3 gene sequence flanked on both sides by 40 bp of the Tg737 exon 2 sequences. With this construct, homologous recombination between the Tg737-SEF and the Tg737 recombinant shuttle vector in yeast should lead to disruption of the Tg737 exon 2 by replacement of the middle 13 bp by the HIS3 sequence (0.9 kb).

In order to generate the targeting construct, yeast strain DG1500 (*Saccharomyces cerevisiae*) incapable of growing on medium lacking histidine was simultaneously transformed with the Tg737 recombinant shuttle plasmid described above (prepared by alkaline lysis) and the Tg737-HIS SEF (FIG. 4) using the method of Geitz et al. (1995). High Efficiency Transformation with Lithium Acetate. In: "Molecular Genetics of Yeast, A Practical Approach, J. R. Jonston, ed., pp. 121–134, which is incorporated herein by reference. Once the shuttle vector is in the cells, the plasmid will recombine with the SEF via the homologous genomic sequences.

Clones containing targeting plasmids resulting from recombination of the Tg737 recombinant shuttle vector and the Tg737-SEF were identified by determining whether HIS3 and the URA3 markers cosegregate, which suggests that the HIS3 marker sequence has been introduced into the shuttle vector. This involves replica plating from his$^-$ plates to ura$^-$ and looking for HIS/URA positive clones (clones which grow on medium lacking histidine and uracil). These and other selection procedures are well known in the art and are described, for example, in *Guide to Yeast Genetics and*

*Molecular Biology*, edited by C. Guthrie and G. R. Fink, vol. 94 in *Methods in Enzymology*, 1991, Academic Press (incorporated herein by reference). If the plasmid doesn't have the HIS marker integrated (if it was integrated into the yeast genome, for example), the plasmid will be lost with high probability through mitotic segregation. However, further studies have shown that the efficiency of homologous recombination is as high as 90%.

Figure 4:
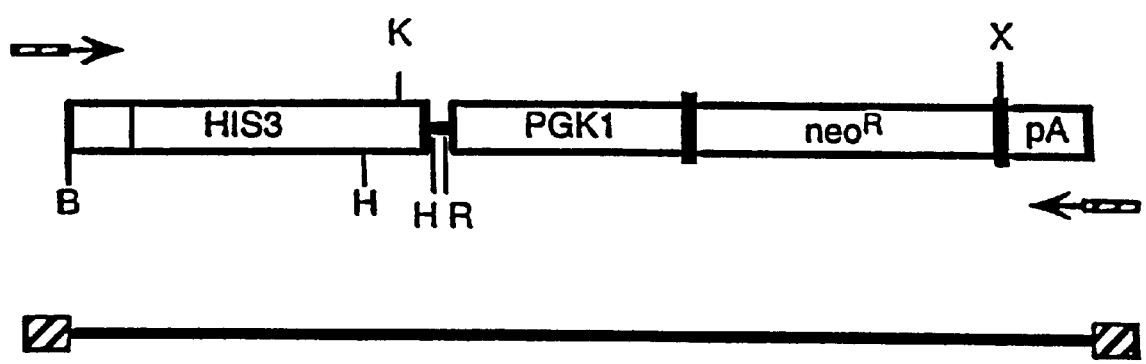
FIG. 4 depicts a specifically engineered fragment (SEF) comprising a HIS-neo cassette.

Mini-preps of total yeast DNA were made from HIS/URA-positive colonies according to the method of Hoffman et al., *Gene*, 57:267–272 (1987) (incorporated herein by reference) and shuttled into XL1-Blue strain of *E. coli* (Stratagene) for plasmid propagation, purification and analysis. Purified plasmids (i.e., targeting constructs) were analyzed via restriction digestion with, for example, EcoRI(R) and PstI. Comparisons of EcoRI (R) and PstI (P) digests of pRS416 and pRS426 carrying the Tg737 HindIII fragment before (−) and after (+) recombination-mediated exon 2 disruption is shown in FIG. 4. Only the expected changes in the restriction pattern (arrows) were observed (i.e., conversion of the wild-type 1.2 kb Eco RI fragment to a 2.1 kb mutant fragment and the wild-type 1.0 kb Pst 1 fragment to mutant 0.15 kb and 1.75 kb fragments), which indicated that the integration event occurred only by homologous recombination. (Note, only the relevant PstI sites are marked on the map.)

PCR amplification of the Tg737 exon 2 using primers described above from the recombined targeting plasmids gave an expected 1 kb fragment compared to a 90 bp fragment amplified from DNA templates with the undisrupted exon 2. PCR analysis of mini-preps of total yeast DNA with the exon 2 specific primers, showed in some cases that there were two PCR fragments, corresponding to both disrupted and undisrupted exon 2, in the same sample. This can be explained by the fact that not all copies of the recombinant shuttle vector in a yeast cell undergo homologous recombination. This was confirmed by electroporating into bacteria plasmid, DNA isolated from two independent yeast clones (I and II), selecting 5 independent bacterial clones derived from each yeast clone and subjecting the plasmids isolating from these clones to restriction analysis. Restriction analysis of the plasmids revealed that all 5 plasmids derived from one of the yeast clones were targeted plasmids, only 3 plasmids from the other yeast clones had the targeted disruption. This result indicates that it is advantageous (but not required) to select a targeted clone in bacteria before proceeding.

EXAMPLE 2

Generation of a His-neo SEF

Preferably, a HIS-neo cassette is used as a template to generate an SEF for disrupting essentially any mouse gene. The 2.5 kb HIS-neo cassette carries the HIS3 yeast gene for selection of the targeting event in yeast and the PGK-neo selection marker for selection of the subsequent targeting event in ES cells. However, other cassettes comprising other markers may be used including a single marker, which may be used for selection in both yeast and ES cells. The His-neo cassette described herein was designed to have some unique restriction sites, which helps in the process of identifying the homologous recombination event in ES cells and transgenic mice.

Figure 3A:
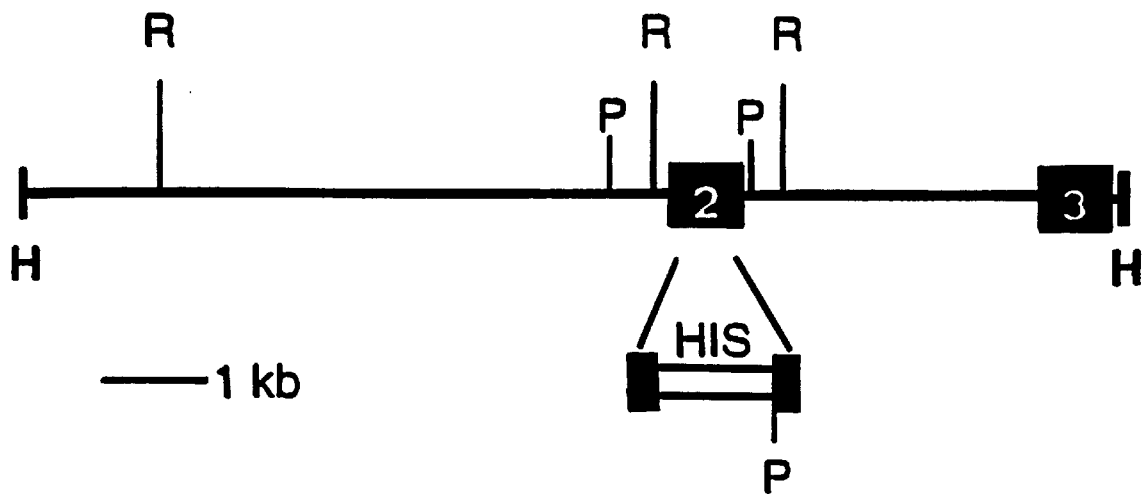
FIG. 3 depicts restriction analysis of recombined targeting plasmids including an agarose gel exhibiting the expected restriction pattern.
Figure 3B:
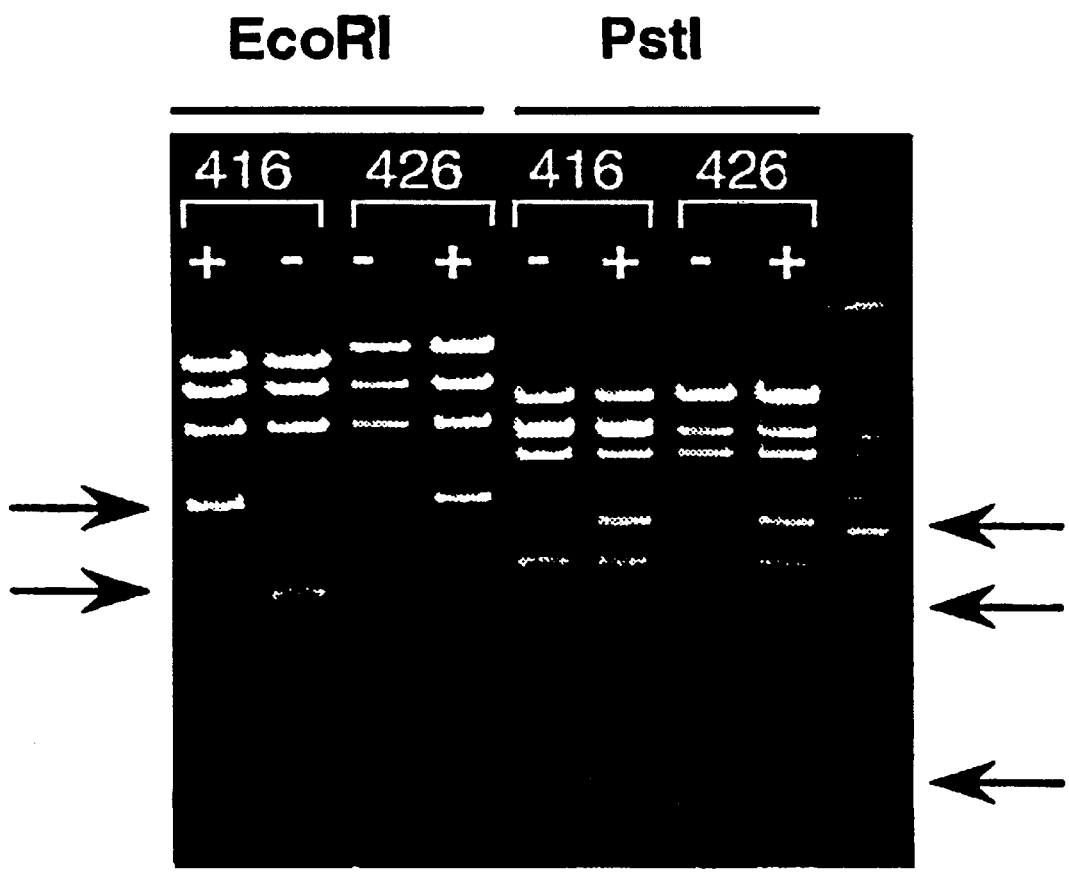

The His-neo marker cassette (FIG. 3) was prepared by subcloning a 0.9 kb BamHI-PstI fragment containing the HIS3 gene into BamHI-PstI digested pBluescript II KS (Stratagene) thereby creating the pHis plasmid. The His-neo cassette was completed by inserting a 1.6 kb Cla I-Xho I fragment containing phosphoglycerate kinase 1 (PGK1) promoter-neo$^r$-bovine growth factor polyA obtained from plasmid pPGK-neo$^r$-bpA into the ClaI-Xho sites of the pHis plasmid. (See, Soriano et al., *Cell*, 64:693–702 [1991].)

The Tg737-HIS-neo SEF (2.6 kb) was derived by PCR using the HIS-neo cassette as a template. Two 60-mer hybrid primers were used to generate this SEF by PCR; the first 40 bp of each primer correspond to the 5' or 3' ends of exon 2 (the same as for the Tg737-HIS-SEF, as described above) and the last 20 bp correspond to the 5' or 3' end of the HIS-neo cassette (see above).

The Tg737-HIS-neo SEF (HIS3-PGK-neo-bGH-polyA sequences flanked on both sides by 40 bp of the Tg737 exon 2 sequences; disruption of the 737 exon 2 by replacement of the middle 13 bp by the HIS-neo) was produced using the following primers (sequence of His-neo given in bold):

```
                                          (SEQ ID NO: 1)
forward primer-same as for 737-HIS SEF (RW 641):

(SEQ ID NO: 3)
while the reverse primer (RW 678):
CTCAGTATCATAGGCTGGGTTGTAGTCGTTGAAACCAGAGC

GCATCCCCAGCATGCCTGC
```

The PCR conditions used were as described above.

Figure 5:
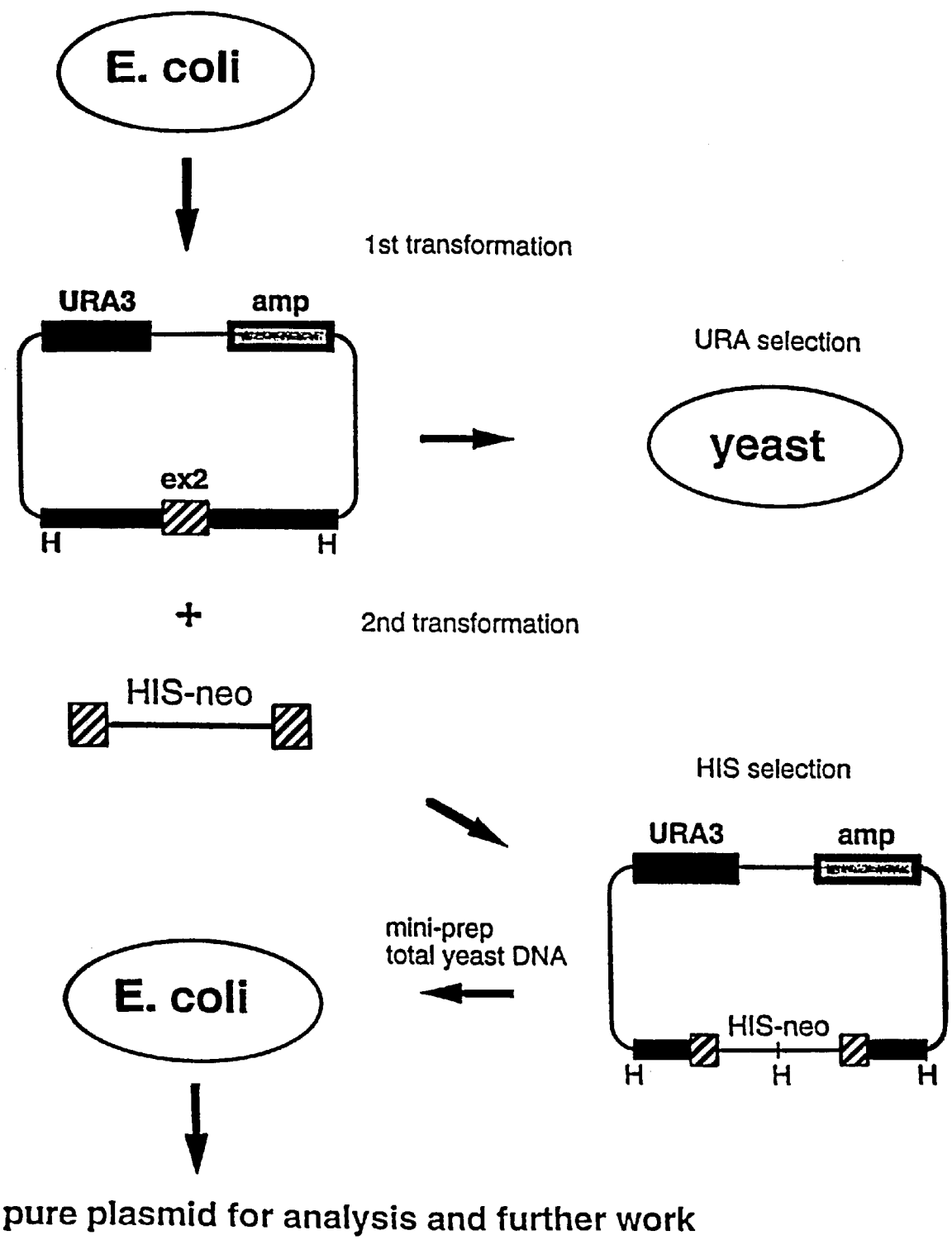
FIG. 5 depicts a scheme for preparing the targeting vectors of the present invention in which the specifically engineered fragment comprises a HIS-neo cassette flanked by exon specific DNA sequences.

The Tg737-HIS-neo SEF was introduced by lithium acetate transformation into yeast (DG1500) already containing the 10.5 kb HindIII fragment of the Tg737 gene in the shuttle vector described above (see FIG. 5). Homologous recombinants were selected with the HIS marker as described above and plasmid DNA isolated from selected colonies was electroporated into *E. coli* for plasmid purification.

Figure 6:
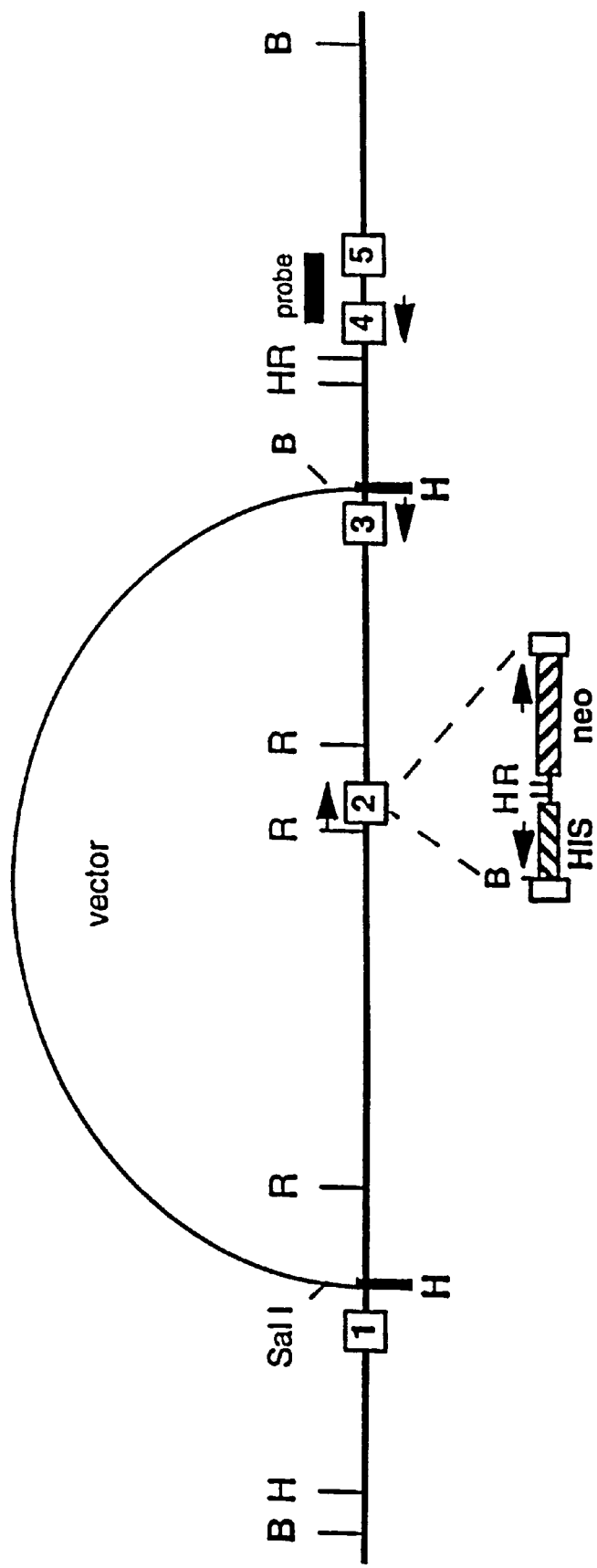
FIG. 6 is a restriction map of the targeting vector inserted into the Tg737 locus.

The recombinant targeting plasmids were analyzed by restriction mapping (not shown) and by PCR (see Example 5 below). PCR analysis with primers specific to exon 2 and to the neighboring exon 3 (FIG. 6) amplified a 4.5 kb fragment from the wild-type genomic clone, and a fragment of the expected size of 7.0 kb was amplified from the HIS-neo-disrupted targeted clone (see FIG. 6). In a parallel analysis where the Tg737-HIS SEF (described above) was used, a fragment of the expected size of 5.5 kb was observed.

EXAMPLE 3

Introduction of Targeting Constructs into ES Cells

For electroporation into ES cells, DNA from the targeting plasmid containing the His-neo cassette and exon 2 specific sequences was purified on a Qiagen (Santa Clarita, Calif.) column and linearized by SalI digestion. Linearized DNA was then introduced into the cells by electroporation using methods described above (Thomas et al., supra; Silva et al., supra, Chen et al., supra; Wang et al., supra; and Knudsen et al., supra. by Fung-Leung et al., *Cell*, 65:443–449 (1991), all incorporated herein by reference). Electroporated cells were then plated on medium containing the antibiotic G418 and G418 resistant colonies were isolated. Genomic DNA was prepared from G418-resistant colonies and was analyzed by Southern blot hybridization and by long-range PCR (see Example 4) as described below for evidence of the integration event. For Southern blot analysis, genomic DNA from G418 resistant ES cells was digested with BamHI and probed with the 0.8 kb fragment marked as a probe in FIG. 6. Integration of the HIS-neo cassette into exon 2 introduced a new BamHI site. The analysis showed that the mutant allele was 13 kb in length as opposed to the corresponding wild-type allele which is 20 kb in length. Among 100 G418 resistant ES cell clones, 6 were found to contain the targeted disruption of exon 2. This targeting efficiency of 6/100 compares favorably with the targeting efficiency in ES cells using constructs produced by cloning in E. coli.

EXAMPLE 4

Detection of Homologous Recombination in ES Cells by Long Range PCR

A scheme to detect the homologous recombination event in ES cells using a long-range PCR approach was developed. This detection scheme is useful because it facilitates screening ES cell clones for recombination event, particularly when unknown genes are to be targeting. For this purpose special PCR primers were designed: the HIS primer, which can be used along with any primer on a 5'-part of a genomic fragment, and the neo-primer, which is used along with a primer on a 3'-part of the fragment (HIS and neo arrows in FIG. 6).

```
                                              (SEQ ID NO: 4)
HIS primer (RW 716):
GTA TAA TTC ATT ATG TGA TAA TGC CAA TCG CTA AG (SEQ ID NO: 5)
neo primer (RW 717):
TGA GGA AAT TGC ATC GCA TTG TCT GAG TAG GTG TC
```

Long-range PCR was performed using a Boehringer Manheim Expand™ Long Template PCR System (Cat #1681842) according to the provider's protocol.

Long-range PCR analysis of genomic DNA from 6 knockout ES clones obtained as described in Example 3 was performed and compared to another clone (#6), where the targeting vector was randomly integrated. The samples were analyzed using a neo primer coupled with a primer in exon 4 and revealed that targeted recombination had occurred in the Tg737 locus while the absence of PCR product in clone #6 confirmed that plasmid integration was random and outside of the Tg737 locus. In another analysis, the same set of samples were amplified using primers specific to exon 2 and exon 4 of the Tg737 gene. This analysis produced a 9 kb band, which corresponds to the insertion-disrupted genomic DNA in addition to the normal 6.5 kb fragment (since the ES cells are heterozygous for the targeted mutation).

EXAMPLE 5

Generation of Tg737 Knockout Mice

Since it was clear that targeted mutations could be generated in ES cells using a vector generated in yeast, cells from one of the ES clones (obtained as described in Example 3) were used for injections into C57 BL/6 blastocysts according to standard methods described in Robertson et al., supra; Bradley et al., supra; and Monsour et al., supra in order to prepare chimeric mice having a disrupted Tg737 gene.

From this experiment a total of 4 chimeric animals were generated and were identified by the agouti coat color. Analysis of DNA derived from the agouti animals was analyzed as described above and found to contain the targeted mutation. Each of these chimeric founder animals is being bred in order to establish the mutation in the germline.

EXAMPLE 6

Generating Knockout Targeting Vector for the Raly Gene

In the experiments described for the Tg737 gene, it was useful to know the restriction map and structure of the gene in order to demonstrate proof of principle. However, such information is not necessary in order to construct targeting vectors according to the present invention.

Figure 7:
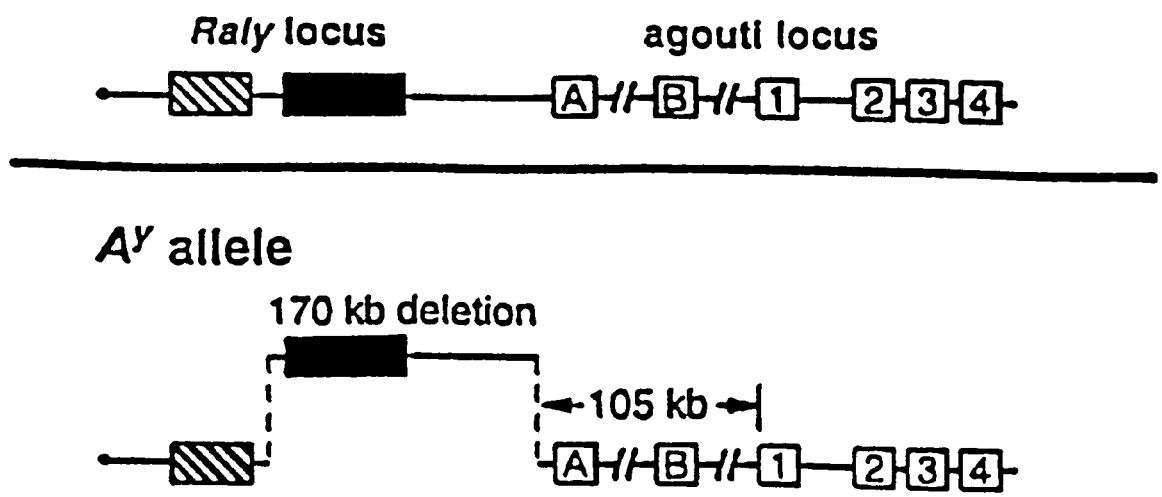
FIG. 7 depicts the wild-type Raly locus and the neighboring agouti locus and depicts the deletion of a 170 kb fragment of DNA that includes the coding portion of the Raly gene.

By way of illustration, the methods of the present invention were utilized to prepare targeting constructs for knocking out the Raly gene in mice. The Raly gene was previously isolated and characterized (see, Michaud et al., Genes & Dev. 7:1203–1213, [1993]). This gene is closely linked with the agouti gene on mouse chromosome 2 and encodes a novel Hn-RNP that is directly associated with the Lethal Yellow mutation of agouti (FIG. 7). (The name Raly is derived from its being an RNP associated with Lethal Yellow.) The Raly cDNA has been cloned and sequenced (FIGS. 8A–C) (SEQ ID NO: 6).

Using homologous recombination in yeast as described in detail above, a targeting vector for the Raly knock-out was created starting from a 129/Sv mouse genomic BAC45C4 (Genome Systems, Huntsville, Ala.) clone which positively hybridized with a Raly cDNA probe (a 224 bp PCR product comprising the 233–457 nt position of the Raly cDNA).

Briefly, an 8.5 kb HindIII genomic fragment of the Raly gene, which hybridizes with the ATG-containing exon, was subcloned from the BAC clone into the pRS426 shuttle vector (described above) giving rise to plasmids pRaly #7 and pRaly #25, which differ only by the orientation of the genomic insert.

At the same time a Raly-SEF was generated by PCR as described above using the HIS-neo cassette (FIG. 4) and described above as a template. For construction of the Raly-HIS-neo SEF (replacement of 124 bp in the ATG-containing exon of Raly by the HIS-neo markers), the following primers were used:

```
                                              (SEQ ID NO: 7)
forward primer (RW 708) (sequence from His-neo cas-
sette in bold):
     TGAACACCATGTCCTTGAAGATTCAGACCAGCAATGTAACT

TGGATCCTCTAGTACACTCT (SEQ ID NO: 8)
reverse primer (RW 709):
     GCTCATTGGCATACTGGACAAAAGCATAGCCTTTGTGCACC

GCATCCCCAGCATGCCTGCT
```

Figure 9:
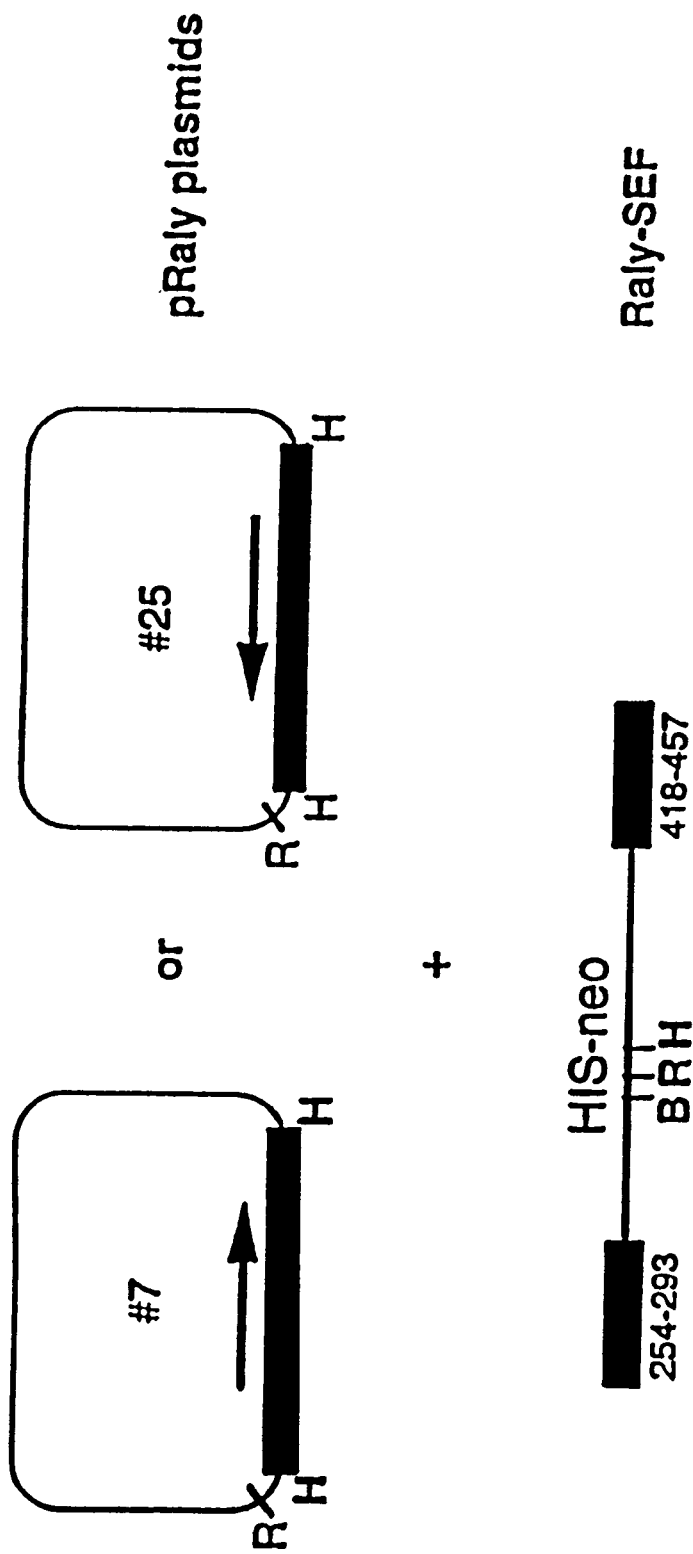
FIG. 9 is a schematic outlining the generation of a knockout plasmid for the Raly gene.

To identify sequences on the same exon for making the Raly-SEF, a conventional PCR analysis with 20-mer primers on genomic and cDNA templates was used. The Raly SEF consisted of the His-neo cassette flanked by nucleotides 254–293 of the Raly cDNA on one side and by nucleotides 418–457 of Raly cDNA on the other side (see FIG. 9). Based on the design of the Raly-SEF, integration of the HIS-neo markers by homologous recombination would delete 124 bp in the ATG-containing exon of Raly (see FIGS. 8A–C).

Figure 10:
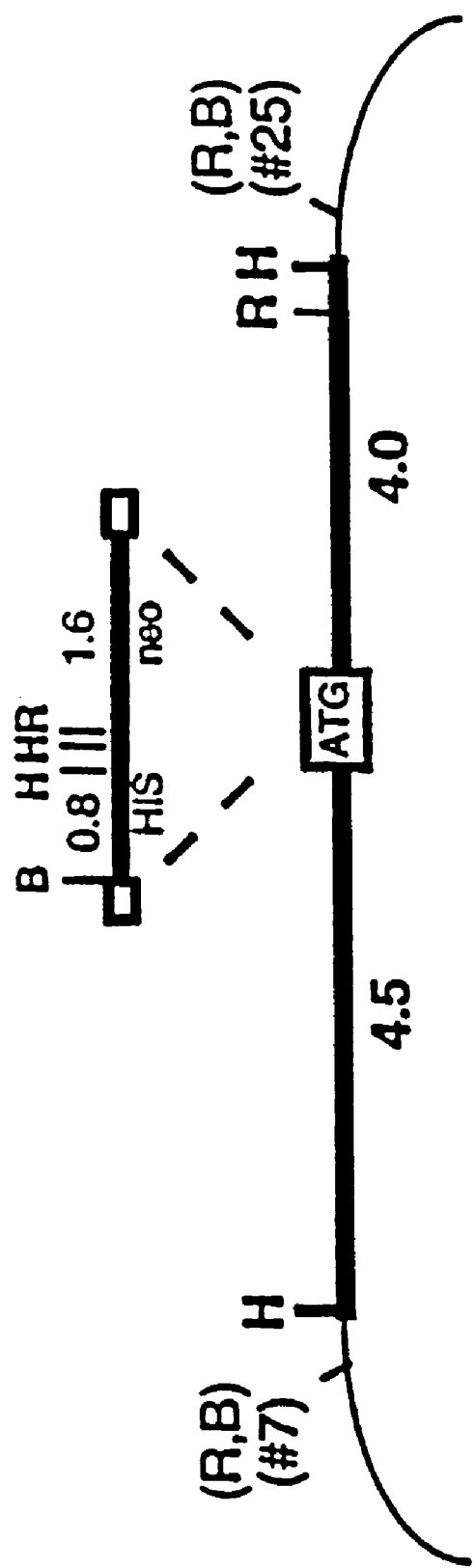
FIG. 10 is a partial restriction map of the Raly SEF and the genomic fragment with which the SEF will recombine homologously.

Yeast transformation was performed using the Raly shuttle vectors described above, and the Raly SEF and DNA from HIS-positive yeast colonies was introduced into E. coli for plasmid DNA isolation and analysis (FIG. 10). Restriction analysis of the targeting plasmids before and after the recombination not only confirmed that the desired recombination took place but also made it possible to map the position of the ATG-containing exon within the HindIII fragment. PCR amplification of targeted Raly fragments from recombinant vectors before (−) and after (+) the recombination in yeast was undertaken and the results are illustrated in FIG. 11. The two right lanes, marked as 680/183, correspond to PCR from cDNA and from genomic (g) DNA using a primer (680) from the targeted site and another primer (183) located outside the targeting vector. These two primers (or the neo primer along with the 183 primer) will be used for testing ES cell clones for homologous recombination.

The foregoing demonstrates that starting with just the sequence of the Raly cDNA and a genomic 129/Sv mouse genomic BAC clone containing part or all of an exon of the Raly, it is possible to generate targeting constructs for the gene in a yeast system.

The foregoing examples were presented by way of illustration and are not intended to limit the scope of the invention as set forth in the appended claims. All of the references cited herein are incorporated by reference.

What is claimed is:

1. A method for preparing gene targeting vectors in yeast, the method comprising:
   a) preparing a shuttle vector comprising a first yeast selectable marker, a bacterial selectable marker and a fragment of genomic DNA containing at least part of a gene to be targeted;
   b) preparing a specific engineered fragment (SEF) comprising a marker cassette, the marker cassette comprising a second yeast selectable marker different from the first yeast selectable marker, a selectable marker capable of expression in mammalian embryonic stem cells said marker cassette being flanked on each side by mammalian gene-specific flanking sequences homologous to a portion of the gene to be targeted;
   c) transforming yeast cells with the shuttle vector of step a) and with the SEF of step b), and allowing said shuttle vector and said SEF to recombine by homologous recombination;
   d) selecting the transformed yeast cells for expression of said first and second yeast selectable markers; and
   e) isolating the targeting vector produced by recombination between the shuttle vector and the SEF from the yeast cells selected in step d).

2. The method of claim 1 wherein said gene-specific flanking sequences each comprise at least about 20 nucleotides.

3. The method of claim 2 wherein said gene-specific flanking sequence each comprise from 40 to about 400 nucleotides.

4. The method of claim 1 wherein said fragment of genomic DNA comprises from about one to about 15 kb.

5. The method of claim 1 wherein said fragment of genomic DNA comprises at least from about 0.5 to about 5 kb of DNA on each side of a site in said gene to be targeted.

6. The method of claim 1 wherein said fragment of genomic DNA comprises at least 1 kb of genomic DNA on each side of a site in a gene to be targeted.

7. The method of claim 1 wherein the first yeast selectable marker of step a) is selected from the group consisting of His, Ura3, and Leu2.

8. The method of claim 1 wherein said bacterial selectable marker is selected from the group consisting of $tet^r$, $amp^r$, $neo^r$, chloramphenol resistance.

9. The method of claim 1 wherein the second yeast selectable marker is selected from the group consisting of His, Ura3, and Leu2.

10. The method of claim 1 wherein said mammalian cell selectable marker is selected from the group consisting of $neo^r$, hygromycin resistant marker and Salmonella his D, and puromycin N-acetyl-transferase.

11. The method of claim 1 wherein said second yeast selectable marker and mammalian cell selectable marker are the same marker.

12. A targeting construct comprising a marker cassette, the marker cassette comprising a first yeast selectable marker and a mammalian cell selectable marker, said cassette being flanked on each side by DNA homologous to a gene to be targeted, said targeting construct further comprising a second yeast selectable marker different from the first yeast selectable marker and a bacterial selectable marker.

13. The targeting construct of claim 12 wherein said DNA homologous to the gene to be targeted comprises from about 1 kb to about 15 kb.

14. The targeting construct of claim 12 wherein said DNA homologous to the gene to be targeted comprises from about 0.5 to about 5 kilobases of DNA on each side of the genomic site to be targeted.

15. The targeting construct of claim 12 or 13 wherein the first yeast selectable marker is selected from the group consisting of His, Ura3, and Leu2.

16. The targeting construct of claim 12, 13 or 14 wherein the second yeast selectable marker is selected from the group consisting of His, Ura3, and Leu2.

17. The targeting vector of claim 12, 13, or 14 wherein the mammalian cell selectable marker is selected from the group consisting of $neo^r$, hygromicin resistance marker, Salmonella his D, and puromycin N-acetyl transferase.

18. The targeting vector of claim 12, 13, or 14 wherein the bacterial selectable marker is selected from the group consisting of $amp^r$, $neo^r$, $tet^r$, chloramphenol resistance.

19. A method of preparing gene targeting constructs in homologous recombination competent cells the method comprising the steps of:
   a) preparing a first DNA construct, the first DNA construct comprising all or part of a gene to be targeted;
   b) preparing a second DNA construct, the second DNA construct comprising a DNA for insertion into a site in a mammalian gene, said DNA for insertion sequence being flanked on both sides by gene-specific sequences homologous to a portion of the gene to be targeted and
   c) introducing into host cells competent to mediate homologous recombination the first and second DNA constructs;
   d) allowing the first and second DNA constructs to recombine via their homologous sequences thereby producing a targeting construct; and
   e) isolating the targeting construct produced in step d).

20. The method of claim 19 wherein said gene-specific flanking sequences each comprise at least 40 to 400 nucleotides.

21. The method of claim 19 wherein said gene-specific flanking sequences each comprise preferably about 40 nucleotides.

22. The method of claim 19 wherein said fragment of genomic DNA comprises from about 1 kbp to about 15 kbp.

23. The method of claim 19 wherein said fragment of genomic DNA comprises from about 0.5 kbp to about 5 kbp on each side of the site in the gene to be targeted.

24. The method of claim 19 wherein said fragment of genomic DNA comprises at least 1 kbp on each side of a site in said gene to be targeted.

25. The targeting vector of claim 15 wherein the mammalian cell selectable marker is selected from the group consisting of $neo^r$, hygromicin resistance marker, Salmonella his D, and puromycin N-acetyl tansferase.

26. The targeting vector of claim 15 wherein the bacterial selectable marker is selected from the group consisting of $amp^r$, $neo^r$, $tet^r$, chloramphenol resistance.

* * * * *